US005312737A

United States Patent [19]

Bolling et al.

[11] Patent Number: 5,312,737

[45] Date of Patent: * May 17, 1994

[54] CKS METHOD OF HCV PROTEIN SYNTHESIS

[75] Inventors: Timothy J. Bolling, Gurnee; Wlodzimierz Mandecki, Libertyville, both of Ill.

[73] Assignee: Abbott Laboratories, Abbott Park, Ill.

[*] Notice: The portion of the term of this patent subsequent to Jun. 23, 2009 has been disclaimed.

[21] Appl. No.: 835,878

[22] Filed: Feb. 14, 1992

Related U.S. Application Data

[63] Continuation-in-part of Ser. No. 573,103, Aug. 24, 1990, abandoned, which is a continuation of Ser. No. 276,263, Nov. 23, 1988, Pat. No. 5,124,255, which is a continuation-in-part of Ser. No. 167,067, Mar. 11, 1988, abandoned.

[51] Int. Cl.[5] .................... C12N 15/00; C12N 15/63; C12N 15/67; C12P 21/06

[52] U.S. Cl. .................... 435/69.3; 435/69.1; 435/69.7; 435/172.3; 435/320.1; 536/23.1; 536/23.4; 935/22; 935/38; 935/47

[58] Field of Search .................... 435/69.3, 69.1, 172.3, 435/320.1; 536/27, 23.1, 23.4

[56] References Cited

U.S. PATENT DOCUMENTS 5,124,255 6/1992 Bolling et al. .................... 435/69.3

OTHER PUBLICATIONS

Szoka et al (1986) DNA 5(1): 11-20.

Goldman et al (1986) J. Biol. Chem. 261(34): 15831-15835.

Ray et al. (1981) J. Bact. 145(3): 1273-1280.

Glasser et al (1987) Proc. Natl. Acad. Sci. USA 84: 4007-4011.

Gatenby et al (1986) Gene 45: 11-18.

Chang et al (1985) Science 228: 93-96.

Gibson et al (1987) Gene 53: 285-286.

*Primary Examiner*—Jacqueline Stone

*Assistant Examiner*—Johnny F. Railey, II

*Attorney, Agent, or Firm*—Daniel W. Collins; James L. Wilcox

[57] ABSTRACT

Disclosed is a method of producing fusion proteins, particularly HCV fusion proteins, wherein one part of the fusion protein is formed from the bacterial protein CKS.

14 Claims, 53 Drawing Sheets

FIG.5
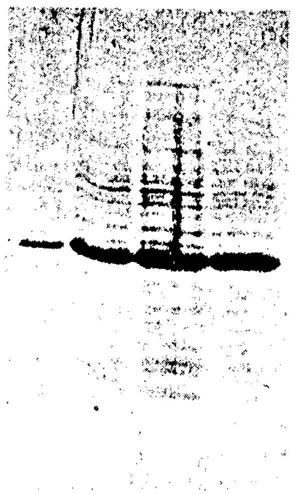
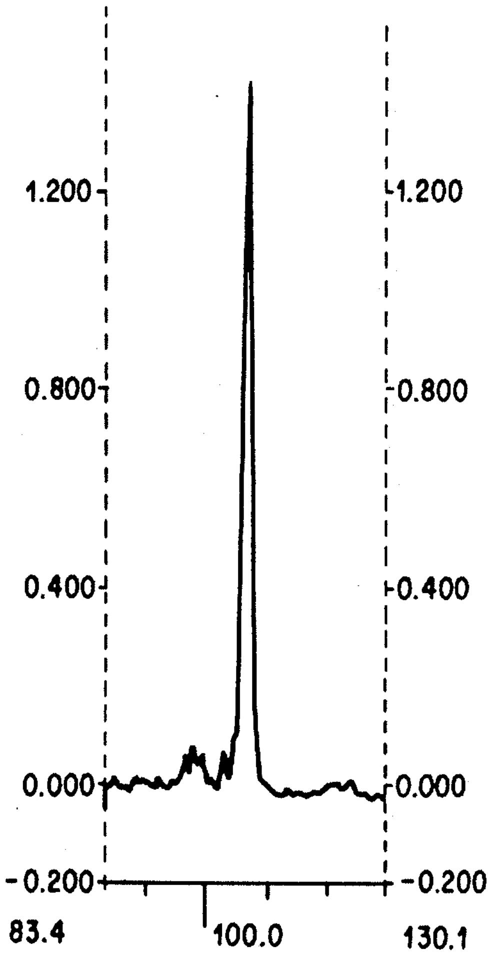
| NO. | Y. POS. | AREA | MARK | % |
|---|---|---|---|---|
| 1 | 83.8 | 6.753 | | 0.0 |
| 2 | 85.1 | 235.503 | | 0.3 |
| 3 | 86.5 | 38.445 | | 0.0 |
| 4 | 88.6 | 513.300 | V | 0.7 |
| 5 | 90.7 | 673.238 | V | 1.0 |
| 6 | 92.8 | 573.726 | V | 0.2 |
| 7 | 94.2 | 101.197 | V | 0.1 |
| 8 | 95.0 | 319.117 | V | 0.4 |
| 9 | 95.7 | 267.394 | V | 0.4 |
| 10 | 96.8 | 1640.438 | V | 2.5 |
| 11 | 98.2 | 1330.840 | V | 2.0 |
| 12 | 99.1 | 908.457 | V | 1.3 |
| 13 | 100.2 | 1297.070 | V | 1.9 |
| 14 | 101.4 | 353.679 | V | 0.5 |
| 15 | 103.1 | 1716.504 | V | 2.6 |
| 16 | 104.8 | 1644.469 | V | 2.5 |
| 17 | 107.4 | 49672.63 | V | 76.4 |
| 18 | 110.8 | 216.800 | | 0.3 |
| 19 | 111.9 | 53.242 | | 0.0 |
| 20 | 112.7 | 46.527 | V | 0.0 |
| 21 | 113.7 | 345.621 | V | 0.5 |
| 22 | 116.0 | 134.054 | | 0.2 |
| 23 | 116.8 | 9.308 | | 0.0 |
| 24 | 117.4 | 28.648 | V | 0.0 |
| 25 | 118.8 | 262.964 | V | 0.4 |
| 26 | 120.5 | 663.109 | V | 1.0 |
| 27 | 122.3 | 917.160 | V | 1.4 |
| 28 | 124.7 | 953.421 | V | 1.4 |
| 29 | 126.8 | 7.957 | | 0.0 |
| 30 | 127.8 | 63.953 | | 0.0 |
| | TOTAL | 64995.53 | | |

FIG. 9-1

```
       BamHI      (NarI)
1   CTCTGGATCCCCGGCGACCCGGGTGGTGGTGACATGCGTGACAACTGGCGTTCTGAACTGTACAAATAC   69
    LeuTrpIleProGlyAspProGlyGlyGlyAspMETArgAspAsnTrpArgSerGluLeuTyrLysTyr
       6

                  INSERT 1
70  AAAGTTGTTAAAATCGAACCGCTGGGTGTTGCTCCGACTAAAGCTAAACGTCGTGTTGTTCAGCGTGAA  138
    LysValValLysIleGluProLeuGlyValAlaProThrLysAlaLysArgArgValValGlnArgGlu

139 AAACGCGCCGTTGGTATCGGTGCACTGTTCCTGGGTTTCCTGGGTGCTGCTGGTTCTACCATGGGTGCT  207
    LysArgAlaValGlyIleGlyAlaLeuPheLeuGlyPheLeuGlyAlaAlaGlySerThrMETGlyAla

208 GCTTCTATGACCCTGACTGTTCAGGCCCGTCAGCTTCTGTCTGGTATCGTTCAGCAGCAGAACAATCTG  276
    AlaSerMETThrLeuThrValGlnAlaArgGlnLeuLeuSerGlyIleValGlnGlnGlnAsnAsnLeu

277 CTGCGTGCTATCGAAGCTCAGCAGCATCTGCTGCAACTGACCGTTTGGGGTATCAAACAGCTTCAGGCT  345
    LeuArgAlaIleGluAlaGlnGlnHisLeuLeuGlnLeuThrValTrpGlyIleLysGlnLeuGlnAla

346 CGTATCCTGGCTGTTGAACGTTACCTGAAAGACCAGCAGCTGCTGGGTATCTGGGGTTGCTCTGGTAAA  414
    ArgIleLeuAlaValGluArgTyrLeuLysAspGlnGlnLeuLeuGlyIleTrpGlyCysSerGlyLys

415 CTGATCTGCACTACTGCTGTTCCGTGGAACGCTTCTTGGTCTAACAAATCTCTGGAACAGATCTGGAAC  483
    LeuIleCysThrThrAlaValProTrpAsnAlaSerTrpSerAsnLysSerLeuGluGlnIleTrpAsn
```

FIG. 9-2

```
484 AACATGACTTGGATGGAATGGGACCGTGAAATCAACAACTACACAAGCTTGATCCACTCTCTGATCGAA 552
    AsnMETThrTrpMETGluTrpAspArgGluIleAsnAsnTyrThrSerLeuIleHisSerLeuIleGlu

                                                                  XbaI
553 GAAAGCCAGAACCAGCAGGAAAAAAACGAACAGGAACTTCTAGAACTGGACAAATGGGCTTCTCTGTGG 621
    GluSerGlnAsnGlnGlnGluLysAsnGluGlnGluLeuLeuGluLeuAspLysTrpAlaSerLeuTrp
                                                                  592

                   INSERT 2
622 AACTGGTTTAACATCACCAACTGGCTGTGGTACATCAAACTGTTCATCATGATCGTTGGTGGTCTGGTT 690
    AsnTrpPheAsnIleThrAsnTrpLeuTrpTyrIleLysLeuPheIleMETIleValGlyGlyLeuVal

                                                              HpaI
691 GGTCTGCGTATCGTTTTCGCTGTTCTGTCTGTTGTTAACCGTGTTCGTCAGGGTTACTCTCCGCTGTCT 759
    GlyLeuArgIleValPheAlaValLeuSerValValAsnArgValArgGlnGlyTyrSerProLeuSer
                                                              727

760 TTCCAGACCCATCTGCCGATCCCGCGTGGTCCGGACCGTCCGGAAGGTATCGAAGAAGAAGgCGGCGAA 828
    PheGlnThrHisLeuProIleProArgGlyProAspArgProGluGlyIleGluGluGluGlyGlyGlu

829 CGTGACCGTGACCGTTCCATtCGTCTGGTAAACGGTTCTCTGGCTCTGATCTGGGACGATCTGCGTTCT 897
    ArgAspArgAspArgSerIleArgLeuValAsnGlySerLeuAlaLeuIleTrpAspAspLeuArgSer
```

FIG. 9-3

```
898  CTGTGCCTGTTCTCTTACCACCGTCTGCGTGATCTGCTGCTGATCGTGACTCGTATCGTTGAACTGCTC  966
     LeuCysLeuPheSerTyrHisArgLeuArgAspLeuLeuLeuIleValThrArgIleValGluLeuLeu

967  GGCCGTCGTGGTTGGGAAGCTCTGAAATACTGGTGGAATCTGCTTCAGTACTGGTCCCAGGAACTGAAA 1035
     GlyArgArgGlyTrpGluAlaLeuLysTyrTrpTrpAsnLeuLeuGlnTyrTrpSerGlnGluLeuLys

1036 AACTCTGCTGTTTCTCTGCTGAACGCTACTGCTATCGCTGTTGCTGAAGGCACCGATCGTGTTATCGAA 1104
     AsnSerAlaValSerLeuLeuAsnAlaThrAlaIleAlaValAlaGluGlyThrAspArgValIleGlu

1105 GTAGTTCAGGGTGCTTACCGTGCTATCCGTCACATtCCGCGTCGTATCCGTCAGGGTCTGGAACGTATC 1173
     ValValGlnGlyAlaTyrArgAlaIleArgHisIleProArgArgIleArgGlnGlyLeuGluArgIle

                                  KpnI
                                   |
1174 CTGCTGTAAGCAGGTGGTACCTGCCG 1199
     LeuLeu
                                  1194
```

```
HindIII      BglII
                                    27                                          54
AGC TTA AAG ATC TAC TCT TCC GCT CAC GGC CGT CAC ACC CGT GGC GTT TTC GTT
Ser Leu Lys Ile Tyr Ser Ser Ala His Gly Arg His Thr Arg Gly Val Phe Val
linker sequences ——|—HIV-2 TMP
                                    81                                          108
CTG GGC TTC CTG GGC TTC CTG GCT ACC GCG GGC TCC GCT ATG GGC GCT GCT TCC
Leu Gly Phe Leu Gly Phe Leu Ala Thr Ala Gly Ser Ala MET Gly Ala Ala Ser

                                    135                                         162
CTG ACC GTT TCC GCT CAG TCC CGT ACC CTG CTG GCT GGC ATC GTT CAG CAG CAG
Leu Thr Val Ser Ala Gln Ser Arg Thr Leu Leu Ala Gly Ile Val Gln Gln Gln

                                    189                                         216
CAG CAA CTT CTA GAC GTT GTT AAA CGT CAG CAG GAG CTC CTG CGT CTG ACC GTT
Gln Gln Leu Leu Asp Val Val Lys Arg Gln Gln Glu Leu Leu Arg Leu Thr Val

                                    243                                         270
TGG GGC ACC AAA AAC CTG CAG GCT CGT GTT ACC GCT ATC GAA AAA TAC CTG CAG
Trp Gly Thr Lys Asn Leu Gln Ala Arg Val Thr Ala Ile Glu Lys Tyr Leu Gln

                                    297                                         324
GAC CAG GCT CGT CTG AAT TCC TGG GGC TGC GCT TTC CGT CAG GTT TGC CAC ACC
Asp Gln Ala Arg Leu Asn Ser Trp Gly Cys Ala Phe Arg Gln Val Cys His Thr

         NcoI  SalI
ACC GTT CCA TGG TCG A
Thr Val Pro Trp Ser
                |—linker———
```

FIG. 14

```
         10         20         30         40         50         60         70
GAATTAATTC CCATTAATGT GAGTTAGCTC ACTCATTAGG CACCCCAGGC TTTACACTTT ATGTTCCGGC

         80         90        100        110        120       129
                                                                >
TCGTATTTTG TGTGGAATTG TGAGCGGATA ACAATTGGGC ATCCAGTAAG GAGGTTTAA ATG
                                                                 MET

    138         147         156         165         174         183
AGT TTT GTG GTC ATT ATT CCC GCG CGC TAC GCG TCG ACG CGT CTG CCC GGT AAA
Ser Phe Val Val Ile Ile Pro Ala Arg Tyr Ala Ser Thr Arg Leu Pro Gly Lys

    192         201         210         219         228         237
CCA TTG GTT GAT ATT AAC GGC AAA CCC ATG ATT GTT CAT GTT CTT GAA CGC GCG
Pro Leu Val Asp Ile Asn Gly Lys Pro MET Ile Val His Val Leu Glu Arg Ala

    246         255         264         273         282         291
CGT GAA TCA GGT GCC GAG CGC ATC ATC GTG GCA ACC GAT CAT GAG GAT GTT GCC
Arg Glu Ser Gly Ala Glu Arg Ile Ile Val Ala Thr Asp His Glu Asp Val Ala

    300         309         318         327         336         345
CGC GCC GTT GAA GCC GCT GGC GGT GAA GTA TGT ATG ACG CGC GCC GAT CAT CAG
Arg Ala Val Glu Ala Ala Gly Gly Glu Val Cys MET Thr Arg Ala Asp His Gln
```

FIG.18A

```
    354         363         372         381         390         399
TCA GGA ACA GAA CGT CTG GCG GAA GTT GTC GAA AAA TGC GCA TTC AGC GAC GAC
Ser Gly Thr Glu Arg Leu Ala Glu Val Val Glu Lys Cys Ala Phe Ser Asp Asp

    408         417         426         435         444         453
ACG GTG ATC GTT AAT GTG CAG GGT GAT GAA CCG ATG ATC CCT GCG ACA ATC ATT
Thr Val Ile Val Asn Val Gln Gly Asp Glu Pro MET Ile Pro Ala Thr Ile Ile

    462         471         480         489         498         507
CGT CAG GTT GCT GAT AAC CTC GCT CAG CGT CAG GTG GGT ATG GCG ACT CTG GCG
Arg Gln Val Ala Asp Asn Leu Ala Gln Arg Gln Val Gly MET Ala Thr Leu Ala

    516         525         534         543         552         561
GTG CCA ATC CAC AAT GCG GAA GAA GCG TTT AAC CCG AAT GCG GTG AAA GTG GTT
Val Pro Ile His Asn Ala Glu Glu Ala Phe Asn Pro Asn Ala Val Lys Val Val

    570         579         588         597         606         615
CTC GAC GCT GAA GGG TAT GCA CTG TAC TTC TCT CGC GCC ACC ATT CCT TGG GAT
Leu Asp Ala Glu Gly Tyr Ala Leu Tyr Phe Ser Arg Ala Thr Ile Pro Trp Asp
```

FIG. 18B

```
    624         633         642         651         660         669
CGT GAT CGT TTT GCA GAA GGC CTT GAA ACC GTT GGC GAT AAC TTC CTG CGT CAT
Arg Asp Arg Phe Ala Glu Gly Leu Glu Thr Val Gly Asp Asn Phe Leu Arg His

    678         687         696         705         714         723
CTT GGT ATT TAT GGC TAC CGT GCA GGC TTT ATC CGT CGT TAC GTC AAC TGG CAG
Leu Gly Ile Tyr Gly Tyr Arg Ala Gly Phe Ile Arg Arg Tyr Val Asn Trp Gln

    732         741         750         759         768         777
CCA AGT CCG TTA GAA CAC ATC GAA ATG TTA GAG CAG CTT CGT GTT CTG TGG TAC
Pro Ser Pro Leu Glu His Ile Glu MET Leu Glu Gln Leu Arg Val Leu Trp Tyr

    786         795         804         813         822         831
GGC GAA AAA ATC CAT GTT GCT GTT GCT CAG GAA GTT CCT GGC ACA GGT GTG GAT
Gly Glu Lys Ile His Val Ala Val Ala Gln Glu Val Pro Gly Thr Gly Val Asp

    840         849         858         867         876         885
ACC CCT GAA GAT CTC GAC CCG TCG ACG AAT TCC ATG TCT ACC AAC CCG AAA CCG
Thr Pro Glu Asp Leu Asp Pro Ser Thr Asn Ser MET Ser Thr Asn Pro Lys Pro
```

FIG. 18C 894 903 912 921 930 939

CAG AAA AAA AAC AAA CGT AAC ACC AAC CGT CGT CCG CAG GAC GTT AAA TTC CCG
Gln Lys Lys Asn Lys Arg Asn Thr Asn Arg Arg Pro Gln Asp Val Lys Phe Pro 948 957 966 975 984 993

GGT GGT GGT CAG ATC GTT GGT GGT GTT TAC CTG CTG CCG CGT CGT GGT CCG CGT
Gly Gly Gly Gln Ile Val Gly Gly Val Tyr Leu Leu Pro Arg Arg Gly Pro Arg 1002 1011 1020 1029 1038 1047

CTG GGT GTT CGT GCT ACG CGT AAA ACC TCT GAA CGT TCT CAG CCG CGT GGG CGT
Leu Gly Val Arg Ala Thr Arg Lys Thr Ser Glu Arg Ser Gln Pro Arg Gly Arg 1056 1065 1074 1083 1092 1101

CGT CAG CCG ATC CCG AAA GCT CGT CGT CCG GAA GGT CGT ACC TGG GCT CAG CCG
Arg Gln Pro Ile Pro Lys Ala Arg Arg Pro Glu Gly Arg Thr Trp Ala Gln Pro 1110 1119 1128 1137 1146 1155

GGT TAC CCG TGG CCG CTG TAC GGT AAC GAA GGT TGC GGT TGG GCT GGT TGG CTG
Gly Tyr Pro Trp Pro Leu Tyr Gly Asn Glu Gly Cys Gly Trp Ala Gly Trp Leu

FIG. 18D

```
1164        1173        1182        1191        1200        1209
CTG TCT CCG CGT GGA TCT CGT CCG TCT TGG GGT CCG ACC GAC CCG CGT CGT CGT
Leu Ser Pro Arg Gly Ser Arg Pro Ser Trp Gly Pro Thr Asp Pro Arg Arg Arg

1218        1227        1236        1245        1254        1263
TCT CGT AAC CTT GGT AAA GTT ATC GAT ACC CTG ACC TGC GGT TTC GCT GAC CTG
Ser Arg Asn Leu Gly Lys Val Ile Asp Thr Leu Thr Cys Gly Phe Ala Asp Leu

1272        1281        1290        1299        1308        1317
                                                                     >
ATG GGT TAC ATA CCG CTG GTT GGA GCT CCG CTG GGT GGT GCT GCT CGT GCT TAA
MET Gly Tyr Ile Pro Leu Val Gly Ala Pro Leu Gly Gly Ala Ala Arg Ala

      1330       1340       1350       1360       1370       1380       1390
CCCATGGATC CTCTAGACTG CAGGCATGCT AAGTAAGTAG ATCTTGAGCG CGTTCGCGCT GAAATGCGCT

      1400       1410       1420       1430       1440       1450       1460
AATTTCACTT CACGACACTT CAGCCAATTT TGGGAGGAGT GTCGTACCGT TACGATTTTC CTCAATTTTT

      1470       1480       1490       1500       1510       1520       1530
CTTTTCAACA ATTGATCTCA TTCAGGTGAC ATCTTTTATA TTGGCGCTCA TTATGAAAGC AGTAGCTTTT

      1540       1550       1560       1570       1580       1590       1600
ATGAGGGTAA TCTGAATGGA ACAGCTGCGT GCCGAATTAA GCCATTTACT GGGCGAAAAA CTCAGTCGTA
```

FIG. 18E

```
      1610       1620       1630       1640       1650       1660       1670
TTGAGTGCGT CAATGAAAAA GCGGATACGG CGTTGTGGGC TTTGTATGAC AGCCAGGGAA ACCCAATGCC

      1680       1690       1700       1710       1720       1730       1740
GTTAATGGCA AGAAGCTTAG CCCGCCTAAT GAGCGGGCTT TTTTTTCGAC GCGAGGCTGG ATGGCCTTCC

      1750       1760       1770       1780       1790       1800       1810
CCATTATGAT TCTTCTCGCT TCCGGCGGCA TCGGGATGCC CGCGTTGCAG GCCATGCTGT CCAGGCAGGT

      1820       1830       1840       1850       1860       1870       1880
AGATGACGAC CATCAGGGAC AGCTTCAAGG ATCGCTCGCG GCTCTTACCA GCCTAACTTC GATCACTGGA

      1890       1900       1910       1920       1930       1940       1950
CCGCTGATCG TCACGGCGAT TTATGCCGCC TCGGCGAGCA CATGGAACGG GTTGGCATGG ATTGTAGGCG

      1960       1970       1980       1990       2000       2010       2020

CCGCCCTATA CCTTGTCTGC CTCCCCGCGT TGCGTCGCGG TGCATGGAGC CGGGCCACCT CGACCTGAAT
      2030       2040       2050       2060       2070       2080       2090

GGAAGCCGGC GGCACCTCGC TAACGGATTC ACCACTCCAA GAATTGGAGC CAATCAATTC TTGCGGAGAA
      2100       2110       2120       2130       2140       2150       2160

CTGTGAATGC GCAAACCAAC CCTTGGCAGA ACATATCCAT CGCGTCCGCC ATCTCCAGCA GCCGCACGCG

      2170       2180       2190       2200       2210       2220       2230
GCGCATCTCG GGCAGCGTTG GGTCCTGGCC ACGGGTGCGC ATGATCGTGC TCCTGTCGTT GAGGACCCGG
```

FIG. 18F

```
      2240       2250       2260       2270       2280       2290       2300
CTAGGCTGGC GGGGTTGCCT TACTGGTTAG CAGAATGAAT CACCGATACG CGAGCGAACG TGAAGCGACT

      2310       2320       2330       2340       2350       2360       2370
GCTGCTGCAA AACGTCTGCG ACCTGAGCAA CAACATGAAT GGTCTTCGGT TTCCGTGTTT CGTAAAGTCT

      2380       2390       2400       2410       2420       2430       2440
GGAAACGCGG AAGTCAGCGC CCTGCACCAT TATGTTCCGG ATCTGCATCG CAGGATGCTG CTGGCTACCC

      2450       2460       2470       2480       2490       2500       2510
TGTGGAACAC CTACATCTGT ATTAACGAAG CGCTTCTTCC GCTTCCTCGC TCACTGACTC GCTGCGCTCG

      2520       2530       2540       2550       2560       2570       2580
GTCGTTCGGC TGCGGCGAGC GGTATCAGCT CACTCAAAGG CGGTAATACG GTTATCCACA GAATCAGGGG

      2590       2600       2610       2620       2630       2640       2650
ATAACGCAGG AAAGAACATG TGAGCAAAAG GCCAGCAAAA GGCCAGGAAC CGTAAAAAGG CCGCGTTGCT

      2660       2670       2680       2690       2700       2710       2720
GGCGTTTTTC CATAGGCTCC GCCCCCCTGA CGAGCATCAC AAAAATCGAC GCTCAAGTCA GAGGTGGCGA

      2730       2740       2750       2760       2770       2780       2790
AACCCGACAG GACTATAAAG ATACCAGGCG TTTCCCCCTG GAAGCTCCCT CGTGCGCTCT CCTGTTCCGA

      2800       2810       2820       2830       2840       2850       2860
CCCTGCCGCT TACCGGATAC CTGTCCGCCT TTCTCCCTTC GGGAAGCGTG GCGCTTTCTC AATGCTCACG
```

FIG. 18G

```
      2870       2880       2890       2900       2910       2920       2930
CTGTAGGTAT CTCAGTTCGG TGTAGGTCGT TCGCTCCAAG CTGGGCTGTG TGCACGAACC CCCCGTTCAG

      2940       2950       2960       2970       2980       2990       3000
CCCGACCGCT GCGCCTTATC CGGTAACTAT CGTCTTGAGT CCAACCCGGT AAGACACGAC TTATCGCCAC

      3010       3020       3030       3040       3050       3060       3070
TGGCAGCAGC CACTGGTAAC AGGATTAGCA GAGCGAGGTA TGTAGGCGGT GCTACAGAGT TCTTGAAGTG

      3080       3090       3100       3110       3120       3130       3140
GTGGCCTAAC TACGGCTACA CTAGAAGGAC AGTATTTGGT ATCTGCGCTC TGCTGAAGCC AGTTACCTTC

      3150       3160       3170       3180       3190       3200       3210
GGAAAAAGAG TTGGTAGCTC TTGATCCGGC AAACAAACCA CCGCTGGTAG CGGTGGTTTT TTTGTTTGCA

      3220       3230       3240       3250       3260       3270       3280
AGCAGCAGAT TACGCGCAGA AAAAAAGGAT CTCAAGAAGA TCCTTTGATC TTTTCTACGG GGTCTGACGC

      3290       3300       3310       3320       3330       3340       3350
TCAGTGGAAC GAAAACTCAC GTTAAGGGAT TTTGGTCATG AGATTATCAA AAAGGATCTT CACCTAGATC

      3360       3370       3380       3390       3400       3410       3420
CTTTTAAATT AAAAATGAAG TTTTAAATCA ATCTAAAGTA TATATGAGTA AACTTGGTCT GACAGTTACC
```

FIG. 18H

| 3430 | 3440 | 3450 | 3460 | 3470 | 3480 | 3490 |
|---|---|---|---|---|---|---|
| AATGCTTAAT | CAGTGAGGCA | CCTATCTCAG | CGATCTGTCT | ATTTCGTTCA | TCCATAGTTG | CCTGACTCCC |
| 3500 | 3510 | 3520 | 3530 | 3540 | 3550 | 3560 |
| CGTCGTGTAG | ATAACTACGA | TACGGGAGGG | CTTACCATCT | GGCCCCAGTG | CTGCAATGAT | ACCGCGAGAC |
| 3570 | 3580 | 3590 | 3600 | 3610 | 3620 | 3630 |
| CCACGCTCAC | CGGCTCCAGA | TTTATCAGCA | ATAAACCAGC | CAGCCGGAAG | GGCCGAGCGC | AGAAGTGGTC |
| 3640 | 3650 | 3660 | 3670 | 3680 | 3690 | 3700 |
| CTGCAACTTT | ATCCGCCTCC | ATCCAGTCTA | TTAATTGTTG | CCGGGAAGCT | AGAGTAAGTA | GTTCGCCAGT |
| 3710 | 3720 | 3730 | 3740 | 3750 | 3760 | 3770 |
| TAATAGTTTG | CGCAACGTTG | TTGCCATTGC | TACAGGCATC | GTGGTGTCAC | GCTCGTCGTT | TGGTATGGCT |
| 3780 | 3790 | 3800 | 3810 | 3820 | 3830 | 3840 |
| TCATTCAGCT | CCGGTTCCCA | ACGATCAAGG | CGAGTTACAT | GATCCCCCAT | GTTGTGCAAA | AAAGCGGTTA |
| 3850 | 3860 | 3870 | 3880 | 3890 | 3900 | 3910 |
| GCTCCTTCGG | TCCTCCGATC | GTTGTCAGAA | GTAAGTTGGC | CGCAGTGTTA | TCACTCATGG | TTATGGCAGC |
| 3920 | 3930 | 3940 | 3950 | 3960 | 3970 | 3980 |
| ACTGCATAAT | TCTCTTACTG | TCATGCCATC | CGTAAGATGC | TTTTCTGTGA | CTGGTGAGTA | CTCAACCAAG |
| 3990 | 4000 | 4010 | 4020 | 4030 | 4040 | 4050 |
| TCATTCTGAG | AATAGTGTAT | GCGGCGACCG | AGTTGCTCTT | GCCCGGCGTC | AACACGGGAT | AATACCGCGC |

FIG. 18I

| 4060 | 4070 | 4080 | 4090 | 4100 | 4110 | 4120 |
|---|---|---|---|---|---|---|
| CACATAGCAG | AACTTTAAAA | GTGCTCATCA | TTGGAAAACG | TTCTTCGGGG | CGAAAACTCT | CAAGGATCTT |
| 4130 | 4140 | 4150 | 4160 | 4170 | 4180 | 4190 |
| ACCGCTGTTG | AGATCCAGTT | CGATGTAACC | CACTCGTGCA | CCCAACTGAT | CTTCAGCATC | TTTTACTTTC |
| 4200 | 4210 | 4220 | 4230 | 4240 | 4250 | 4260 |
| ACCAGCGTTT | CTGGGTGAGC | AAAAACAGGA | AGGCAAAATG | CCGCAAAAAA | GGGAATAAGG | GCGACACGGA |
| 4270 | 4280 | 4290 | 4300 | 4310 | 4320 | 4330 |
| AATGTTGAAT | ACTCATACTC | TTCCTTTTTC | AATATTATTG | AAGCATTTAT | CAGGGTTATT | GTCTCATGAG |
| 4340 | 4350 | 4360 | 4370 | 4380 | 4390 | 4400 |
| CGGATACATA | TTTGAATGTA | TTTAGAAAAA | TAAACAAATA | GGGGTTCCGC | GCACATTTCC | CCGAAAAGTG |
| 4410 | 4420 | 4430 | 4440 | 4450 | 4460 | 4470 |
| CCACCTGACG | TCTAAGAAAC | CATTATTATC | ATGACATTAA | CCTATAAAAA | TAGGCGTATC | ACGAGGCCCT |
| 4480 | | | | | | |
| TTCGTCTTCA | A | | | | | |

FIG. 18 J

```
        10         20         30         40         50         60         70
GAATTAATTC CCATTAATGT GAGTTAGCTC ACTCATTAGG CACCCCAGGC TTTACACTTT ATGTTCCGGC

        80         90        100        110        120       129
                                                                >
TCGTATTTTG TGTGGAATTG TGAGCGGATA ACAATTGGGC ATCCAGTAAG GAGGTTTAA ATG
                                                                  MET

    138         147         156         165         174         183
AGT TTT GTG GTC ATT ATT CCC GCG CGC TAC GCG TCG ACG CGT CTG CCC GGT AAA
Ser Phe Val Val Ile Ile Pro Ala Arg Tyr Ala Ser Thr Arg Leu Pro Gly Lys

    192         201         210         219         228         237
CCA TTG GTT GAT ATT AAC GGC AAA CCC ATG ATT GTT CAT GTT CTT GAA CGC GCG
Pro Leu Val Asp Ile Asn Gly Lys Pro MET Ile Val His Val Leu Glu Arg Ala

    246         255         264         273         282         291
CGT GAA TCA GGT GCC GAG CGC ATC ATC GTG GCA ACC GAT CAT GAG GAT GTT GCC
Arg Glu Ser Gly Ala Glu Arg Ile Ile Val Ala Thr Asp His Glu Asp Val Ala

    300         309         318         327         336         345
CGC GCC GTT GAA GCC GCT GGC GGT GAA GTA TGT ATG ACG CGC GCC GAT CAT CAG
Arg Ala Val Glu Ala Ala Gly Gly Glu Val Cys MET Thr Arg Ala Asp His Gln
```

FIG. 24A

```
     354               363               372               381               390               399
TCA GGA ACA GAA CGT CTG GCG GAA GTT GTC GAA AAA TGC GCA TTC AGC GAC GAC
Ser Gly Thr Glu Arg Leu Ala Glu Val Val Glu Lys Cys Ala Phe Ser Asp Asp

     408               417               426               435               444               453
ACG GTG ATC GTT AAT GTG CAG GGT GAT GAA CCG ATG ATC CCT GCG ACA ATC ATT
Thr Val Ile Val Asn Val Gln Gly Asp Glu Pro MET Ile Pro Ala Thr Ile Ile

     462               471               480               489               498               507
CGT CAG GTT GCT GAT AAC CTC GCT CAG CGT CAG GTG GGT ATG GCG ACT CTG GCG
Arg Gln Val Ala Asp Asn Leu Ala Gln Arg Gln Val Gly MET Ala Thr Leu Ala

     516               525               534               543               552               561
GTG CCA ATC CAC AAT GCG GAA GAA GCG TTT AAC CCG AAT GCG GTG AAA GTG GTT
Val Pro Ile His Asn Ala Glu Glu Ala Phe Asn Pro Asn Ala Val Lys Val Val

     570               579               588               597               606               615
CTC GAC GCT GAA GGG TAT GCA CTG TAC TTC TCT CGC GCC ACC ATT CCT TGG GAT
Leu Asp Ala Glu Gly Tyr Ala Leu Tyr Phe Ser Arg Ala Thr Ile Pro Trp Asp
```

FIG. 24B 624 633 642 651 660 669
CGT GAT CGT TTT GCA GAA GGC CTT GAA ACC GTT GGC GAT AAC TTC CTG CGT CAT
Arg Asp Arg Phe Ala Glu Gly Leu Glu Thr Val Gly Asp Asn Phe Leu Arg His 678 687 696 705 714 723
CTT GGT ATT TAT GGC TAC CGT GCA GGC TTT ATC CGT CGT TAC GTC AAC TGG CAG
Leu Gly Ile Tyr Gly Tyr Arg Ala Gly Phe Ile Arg Arg Tyr Val Asn Trp Gln 732 741 750 759 768 777
CCA AGT CCG TTA GAA CAC ATC GAA ATG TTA GAG CAG CTT CGT GTT CTG TGG TAC
Pro Ser Pro Leu Glu His Ile Glu MET Leu Glu Gln Leu Arg Val Leu Trp Tyr 786 795 804 813 822 831
GGC GAA AAA ATC CAT GTT GCT GTT GCT CAG GAA GTT CCT GGC ACA GGT GTG GAT
Gly Glu Lys Ile His Val Ala Val Ala Gln Glu Val Pro Gly Thr Gly Val Asp 840 849 858 867 876 885
ACC CCT GAA GAT CTC GAC CCG TCG ACG AAT TCC ATG GCT GTT GAC TTT ATC CCG
Thr Pro Glu Asp Leu Asp Pro Ser Thr Asn Ser MET Ala Val Asp Phe Ile Pro

FIG. 24C

```
    894         903         912         921         930         939
GTT GAA AAT CTC GAG ACT ACT ATG CGT TCT CCG GTT TTC ACT GAC AAC TCT TCT
Val Glu Asn Leu Glu Thr Thr MET Arg Ser Pro Val Phe Thr Asp Asn Ser Ser

    948         957         966         975         984         993
CCG CCG GTT GTT CCG CAG TCT TTC CAG GTT GCT CAC CTG CAT GCT CCG ACT GGT
Pro Pro Val Val Pro Gln Ser Phe Gln Val Ala His Leu His Ala Pro Thr Gly

   1002        1011        1020        1029        1038        1047
TCT GGT AAA TCT ACT AAA GTT CCA GCT GCT TAC GCT GCT CAG GGT TAC AAA GTT
Ser Gly Lys Ser Thr Lys Val Pro Ala Ala Tyr Ala Ala Gln Gly Tyr Lys Val

   1056        1065        1074        1083        1092        1101
CTG GTT CTG AAC CCG TCT GTT GCT GCT ACT CTG GGT TTC GGC GCC TAC ATG TCT
Leu Val Leu Asn Pro Ser Val Ala Ala Thr Leu Gly Phe Gly Ala Tyr MET Ser

   1110        1119        1128        1137        1146        1155
AAA GCT CAC GGT ATC GAC CCG AAC ATT CGT ACT GGT GTA CGT ACT ATC ACT ACT
Lys Ala His Gly Ile Asp Pro Asn Ile Arg Thr Gly Val Arg Thr Ile Thr Thr
```

FIG. 24 D

```
1164            1173            1182            1191            1200            1209
GGT TCT CCG ATC ACT TAC TCT ACT TAC GGT AAA TTC CTG GCT GAC GGT GGT TGC
Gly Ser Pro Ile Thr Tyr Ser Thr Tyr Gly Lys Phe Leu Ala Asp Gly Gly Cys

1218            1227            1236            1245            1254            1263
TCT GGT GGT GCT TAC GAT ATC ATC ATC TGC GAC GAA TGC CAC TCT ACT GAC GCT
Ser Gly Gly Ala Tyr Asp Ile Ile Ile Cys Asp Glu Cys His Ser Thr Asp Ala

1272            1281            1290            1299            1308            1317
ACT TCT ATC CTG GGT ATC GGT ACC GTT CTG GAC CAG GCT GAA ACT GCA GGT GCT
Thr Ser Ile Leu Gly Ile Gly Thr Val Leu Asp Gln Ala Glu Thr Ala Gly Ala

1326            1335            1344            1353            1362            1371
CGT CTG GTT GTT CTG GCT ACT GCT ACT CCG CCG GGT TCT GTT ACT GTT CCG CAC
Arg Leu Val Val Leu Ala Thr Ala Thr Pro Pro Gly Ser Val Thr Val Pro His

1380            1389            1398            1407            1416            1425
CCG AAC ATC GAA GAA GTT GCT CTG TCG ACT ACT GGT GAA ATC CCG TTC TAC GGT
Pro Asn Ile Glu Glu Val Ala Leu Ser Thr Thr Gly Glu Ile Pro Phe Tyr Gly
```

FIG. 24E

```
1434        1443        1452        1461        1470        1479
AAA GCT ATC CCG CTC GAG GTT ATC AAA GGT GGT CGT CAC CTG ATT TTC TGC CAC
Lys Ala Ile Pro Leu Glu Val Ile Lys Gly Gly Arg His Leu Ile Phe Cys His

1488        1497        1506        1515        1524        1533
TCT AAA AAA AAA TGC GAC GAA CTG GCT GCT AAG CTT GTT GCT CTG GGT ATC AAC
Ser Lys Lys Lys Cys Asp Glu Leu Ala Ala Lys Leu Val Ala Leu Gly Ile Asn

1542        1551        1560        1569        1578        1587
GCT GTT GCT TAC TAC CGT GGT CTG GAC GTT TCT GTT ATC CCG ACT TCT GGT GAC
Ala Val Ala Tyr Tyr Arg Gly Leu Asp Val Ser Val Ile Pro Thr Ser Gly Asp

1596        1605        1614        1623        1632        1641
GTT GTT GTT GTG GCC ACT GAC GCT CTG ATG ACT GGT TAC ACT GGT GAC TTC GAC
Val Val Val Val Ala Thr Asp Ala Leu MET Thr Gly Tyr Thr Gly Asp Phe Asp

1650        1659        1668        1677        1686        1695
TCT GTT ATC GAT TGC AAC ACT TGC AAT TCG TCG ACC GGT TGC GTT GTT ATC GTT
Ser Val Ile Asp Cys Asn Thr Cys Asn Ser Ser Thr Gly Cys Val Val Ile Val
```

FIG. 24F

```
1704                1713                1722                1731                1740                1749
GGT CGT GTT GTT CTG TCT GGT AAA CCG GCC ATT ATC CCG GAC CGT GAA GTT CTG
Gly Arg Val Val Leu Ser Gly Lys Pro Ala Ile Ile Pro Asp Arg Glu Val Leu

1758                1767                1776                1785                1794                1803
TAC CGT GAG TTC GAC GAA ATG GAA GAA TGC TCT CAG CAC CTG CCG TAC ATC GAA
Tyr Arg Glu Phe Asp Glu MET Glu Glu Cys Ser Gln His Leu Pro Tyr Ile Glu

1812                1821                1830                1839                1848                1857
CAG GGT ATG ATG CTG GCT GAA CAG TTC AAA CAG AAA GCT CTG GGT CTG CTG CAG
Gln Gly MET MET Leu Ala Glu Gln Phe Lys Gln Lys Ala Leu Gly Leu Leu Gln

1866                1875                1884                1893                1902                1911
ACC GCT TCT CGT CAG GCT GAA GTT ATC GCT CCG GCT GTT CAG ACC AAC TGG CAG
Thr Ala Ser Arg Gln Ala Glu Val Ile Ala Pro Ala Val Gln Thr Asn Trp Gln

1920                1929                1938                1947                1956                1965
AAA CTC GAG ACC TTC TGG GCT AAA CAC ATG TGG AAC TTC ATC TCT GGT ATC CAG
Lys Leu Glu Thr Phe Trp Ala Lys His MET Trp Asn Phe Ile Ser Gly Ile Gln
```

FIG. 24G

```
    1974                1983                1992                2001                2010                2019
TAC CTG GCT GGT CTG TCT ACC CTG CCG GGT AAC CCG GCT ATC GCA AGC TTG ATG
Tyr Leu Ala Gly Leu Ser Thr Leu Pro Gly Asn Pro Ala Ile Ala Ser Leu MET

    2028                2037                2046                2055                2064                2073
GCT TTC ACC GCT GCT GTT ACC TCT CCG CTG ACC ACC TCT CAG ACC CTG CTG TTC
Ala Phe Thr Ala Ala Val Thr Ser Pro Leu Thr Thr Ser Gln Thr Leu Leu Phe

    2082                2091                2100                2109                2118                2127
AAC ATT CTG GGT GGT TGG GTT GCT GCT CAG CTG GCT GCT CCG GGT GCT GCT ACC
Asn Ile Leu Gly Gly Trp Val Ala Ala Gln Leu Ala Ala Pro Gly Ala Ala Thr

    2136                2145                2154                2163                2172                2181
GCT TTC GTT GGT GCT GGT CTG GCT GGT GCT GCT ATC GGT TCT GTA GGC CTG GGT
Ala Phe Val Gly Ala Gly Leu Ala Gly Ala Ala Ile Gly Ser Val Gly Leu Gly

    2190                2199                2208                2217                2226                2235
AAA GTT CTG ATC GAC ATT CTG GCT GGT TAC GGT GCT GGT GTT GCT GGA GCT CTG
Lys Val Leu Ile Asp Ile Leu Ala Gly Tyr Gly Ala Gly Val Ala Gly Ala Leu
```

FIG. 24H

```
2244           2253           2262           2271           2280           2289
GTT GCT TTC AAA ATC ATG TCT GGT GAA GTT CCG TCT ACC GAA GAT CTG GTT AAC
Val Ala Phe Lys Ile MET Ser Gly Glu Val Pro Ser Thr Glu Asp Leu Val Asn

2298           2307           2316           2325           2334           2343
CTG CTG CCG GCT ATC CTG TCT CCG GGT GCT CTG GTT GTT GGT GTT GTT TGC GCT
Lau Leu Pro Ala Ile Leu Ser Pro Gly Ala Leu Val Val Gly Val Val Cys Ala

2352           2361           2370           2379           2388           2397
GCT ATC CTG CGT CGT CAC GTT GGC CCG GGT GAA GGT GCT GTT CAG TGG ATG AAC
Ala Ile Leu Arg Arg His Val Gly Pro Gly Glu Gly Ala Val Gln Trp MET Asn

2406           2415           2424           2433           2442           2451
CGT CTG ATC GCT TTC GCT TCT CGT GGT AAC CAC GTT TCT CCA TGG GAT CCT CTA
Arg Leu Ile Ala Phe Ala Ser Arg Gly Asn His Val Ser Pro Trp Asp Pro Leu

2460           2469                    2485       2495       2505       2515
                           >
GAC TGC AGG CAT GCT AAG TAA GTAGATCTTG AGCGCGTTCG CGCTGAAATG CGCTAATTTC
Asp Cys Arg His Ala Lys
```

FIG. 24I

| | | | | | | |
|---|---|---|---|---|---|---|
| 2525 | 2535 | 2545 | 2555 | 2565 | 2575 | 2585 |
| ACTTCACGAC | ACTTCAGCCA | ATTTTGGGAG | GAGTGTCGTA | CCGTTACGAT | TTTCCTCAAT | TTTTCTTTTC |
| 2595 | 2605 | 2615 | 2625 | 2635 | 2645 | 2655 |
| AACAATTGAT | CTCATTCAGG | TGACATCTTT | TATATTGGCG | CTCATTATGA | AAGCAGTAGC | TTTTATGAGG |
| 2665 | 2675 | 2685 | 2695 | 2705 | 2715 | 2725 |
| GTAATCTGAA | TGGAACAGCT | GCGTGCCGAA | TTAAGCCATT | TACTGGGCGA | AAAACTCAGT | CGTATTGAGT |
| 2735 | 2745 | 2755 | 2765 | 2775 | 2785 | 2795 |
| GCGTCAATGA | AAAAGCGGAT | ACGGCGTTGT | GGGCTTTGTA | TGACAGCCAG | GGAAACCCAA | TGCCGTTAAT |
| 2805 | 2815 | 2825 | 2835 | 2845 | 2855 | 2865 |
| GGCAAGAAGC | TTAGCCCGCC | TAATGAGCGG | GCTTTTTTTT | CGACGCGAGG | CTGGATGGCC | TTCCCCATTA |
| 2875 | 2885 | 2895 | 2905 | 2915 | 2925 | 2935 |
| TGATTCTTCT | CGCTTCCGGC | GGCATCGGGA | TGCCCGCGTT | GCAGGCCATG | CTGTCCAGGC | AGGTAGATGA |
| 2945 | 2955 | 2965 | 2975 | 2985 | 2995 | 3005 |
| CGACCATCAG | GGACAGCTTC | AAGGATCGCT | CGCGGCTCTT | ACCAGCCTAA | CTTCGATCAC | TGGACCGCTG |
| 3015 | 3025 | 3035 | 3045 | 3055 | 3065 | 3075 |
| ATCGTCACGG | CGATTTATGC | CGCCTCGGCG | AGCACATGGA | ACGGGTTGGC | ATGGATTGTA | GGCGCCGCCC |
| 3085 | 3095 | 3105 | 3115 | 3125 | 3135 | 3145 |
| TATACCTTGT | CTGCCTCCCC | GCGTTGCGTC | GCGGTGCATG | GAGCCGGGCC | ACCTCGACCT | GAATGGAAGC |

FIG. 24J

| 3155 | 3165 | 3175 | 3185 | 3195 | 3205 | 3215 |
|---|---|---|---|---|---|---|
| CGGCGGCACC | TCGCTAACGG | ATTCACCACT | CCAAGAATTG | GAGCCAATCA | ATTCTTGCGG | AGAACTGTGA |
| **3225** | **3235** | **3245** | **3255** | **3265** | **3275** | **3285** |
| ATGCGCAAAC | CAACCCTTGG | CAGAACATAT | CCATCGCGTC | CGCCATCTCC | AGCAGCCGCA | CGCGGCGCAT |
| **3295** | **3305** | **3315** | **3325** | **3335** | **3345** | **3355** |
| CTCGGGCAGC | GTTGGGTCCT | GGCCACGGGT | GCGCATGATC | GTGCTCCTGT | CGTTGAGGAC | CCGGCTAGGC |
| **3365** | **3375** | **3385** | **3395** | **3405** | **3415** | **3425** |
| TGGCGGGGTT | GCCTTACTGG | TTAGCAGAAT | GAATCACCGA | TACGCGAGCG | AACGTGAAGC | GACTGCTGCT |
| **3435** | **3445** | **3455** | **3465** | **3475** | **3485** | **3495** |
| GCAAAACGTC | TGCGACCTGA | GCAACAACAT | GAATGGTCTT | CGGTTTCCGT | GTTTCGTAAA | GTCTGGAAAC |
| **3505** | **3515** | **3525** | **3535** | **3545** | **3555** | **3565** |
| GCGGAAGTCA | GCGCCCTGCA | CCATTATGTT | CCGGATCTGC | ATCGCAGGAT | GCTGCTGGCT | ACCCTGTGGA |
| **3575** | **3585** | **3595** | **3605** | **3615** | **3625** | **3635** |
| ACACCTACAT | CTGTATTAAC | GAAGCGCTTC | TTCCGCTTCC | TCGCTCACTG | ACTCGCTGCG | CTCGGTCGTT |
| **3645** | **3655** | **3665** | **3675** | **3685** | **3695** | **3705** |
| CGGCTGCGGC | GAGCGGTATC | AGCTCACTCA | AAGGCGGTAA | TACGGTTATC | CACAGAATCA | GGGGATAACG |
| **3715** | **3725** | **3735** | **3745** | **3755** | **3765** | **3775** |
| CAGGAAAGAA | CATGTGAGCA | AAAGGCCAGC | AAAAGGCCAG | GAACCGTAAA | AAGGCCGCGT | TGCTGGCGTT |

FIG. 24K

```
      3785       3795       3805       3815       3825       3835       3845
TTTCCATAGG CTCCGCCCCC CTGACGAGCA TCACAAAAAT CGACGCTCAA GTCAGAGGTG GCGAAACCCG

      3855       3865       3875       3885       3895       3905       3915
ACAGGACTAT AAAGATACCA GGCGTTTCCC CCTGGAAGCT CCCTCGTGCG CTCTCCTGTT CCGACCCTGC

      3925       3935       3945       3955       3965       3975       3985
CGCTTACCGG ATACCTGTCC GCCTTTCTCC CTTCGGGAAG CGTGGCGCTT TCTCAATGCT CACGCTGTAG

      3995       4005       4015       4025       4035       4045       4055
GTATCTCAGT TCGGTGTAGG TCGTTCGCTC CAAGCTGGGC TGTGTGCACG AACCCCCCGT TCAGCCCGAC

      4065       4075       4085       4095       4105       4115       4125
CGCTGCGCCT TATCCGGTAA CTATCGTCTT GAGTCCAACC CGGTAAGACA CGACTTATCG CCACTGGCAG

      4135       4145       4155       4165       4175       4185       4195
CAGCCACTGG TAACAGGATT AGCAGAGCGA GGTATGTAGG CGGTGCTACA GAGTTCTTGA AGTGGTGGCC

      4205       4215       4225       4235       4245       4255       4265
TAACTACGGC TACACTAGAA GGACAGTATT TGGTATCTGC GCTCTGCTGA AGCCAGTTAC CTTCGGAAAA

      4275       4285       4295       4305       4315       4325       4335
AGAGTTGGTA GCTCTTGATC CGGCAAACAA ACCACCGCTG GTAGCGGTGG TTTTTTTGTT TGCAAGCAGC

      4345       4355       4365       4375       4385       4395       4405
AGATTACGCG CAGAAAAAAA GGATCTCAAG AAGATCCTTT GATCTTTTCT ACGGGGTCTG ACGCTCAGTG
```

FIG. 24L

```
      4415       4425       4435       4445       4455       4465       4475
GAACGAAAAC TCACGTTAAG GGATTTTGGT CATGAGATTA TCAAAAAGGA TCTTCACCTA GATCCTTTTA

      4485       4495       4505       4515       4525       4535       4545
AATTAAAAAT GAAGTTTTAA ATCAATCTAA AGTATATATG AGTAAACTTG GTCTGACAGT TACCAATGCT

      4555       4565       4575       4585       4595       4605       4615
TAATCAGTGA GGCACCTATC TCAGCGATCT GTCTATTTCG TTCATCCATA GTTGCCTGAC TCCCCGTCGT

      4625       4635       4645       4655       4665       4675       4685
GTAGATAACT ACGATACGGG AGGGCTTACC ATCTGGCCCC AGTGCTGCAA TGATACCGCG AGACCCACCC

      4695       4705       4715       4725       4735       4745       4755
TCACCGGCTC CAGATTTATC AGCAATAAAC CAGCCAGCCG GAAGGGCCGA GCGCAGAAGT GGTCCTGCAA

      4765       4775       4785       4795       4805       4815       4825
CTTTATCCGC CTCCATCCAG TCTATTAATT GTTGCCGGGA AGCTAGAGTA AGTAGTTCGC CAGTTAATAG

      4835       4845       4855       4865       4875       4885       4895
TTTGCGCAAC GTTGTTGCCA TTGCTACAGG CATCGTGGTG TCACGCTCGT CGTTTGGTAT GGCTTCATTC

      4905       4915       4925       4935       4945       4955       4965
AGCTCCGGTT CCCAACGATC AAGGCGAGTT ACATGATCCC CCATGTTGTG CAAAAAAGCG GTTAGCTCCT

      4975       4985       4995       5005       5015       5025       5035
TCGGTCCTCC GATCGTTGTC AGAAGTAAGT TGGCCGCAGT GTTATCACTC ATGGTTATGG CAGCACTGCA
```

FIG. 24M

```
         5045       5055       5065       5075       5085       5095       5105
TAATTCTCTT ACTGTCATGC CATCCGTAAG ATGCTTTTCT GTGACTGGTG AGTACTCAAC CAAGTCATTC

         5115       5125       5135       5145       5155       5165       5175
TGAGAATAGT GTATGCGGCG ACCGAGTTGC TCTTGCCCGG CGTCAACACG GGATAATACC GCGCCACATA

         5185       5195       5205       5215       5225       5235       5245
GCAGAACTTT AAAAGTGCTC ATCATTGGAA AACGTTCTTC GGGGCGAAAA CTCTCAAGGA TCTTACCGCT

         5255       5265       5275       5285       5295       5305       5315
GTTGAGATCC AGTTCGATGT AACCCACTCG TGCACCCAAC TGATCTTCAG CATCTTTTAC TTTCACCAGC

         5325       5335       5345       5355       5365       5375       5385
GTTTCTGGGT GAGCAAAAAC AGGAAGGCAA AATGCCGCAA AAAAGGGAAT AAGGGCGACA CGGAAATGTT

         5395       5405       5415       5425       5435       5445       5455
GAATACTCAT ACTCTTCCTT TTTCAATATT ATTGAAGCAT TTATCAGGGT TATTGTCTCA TGAGCGGATA

         5465       5475       5485       5495       5505       5515       5525
CATATTTGAA TGTATTTAGA AAAATAAACA AATAGGGGTT CCGCGCACAT TTCCCCGAAA AGTGCCACCT

         5535       5545       5555       5565       5575       5585       5595
GACGTCTAAG AAACCATTAT TATCATGACA TTAACCTATA AAAATAGGCG TATCACGAGG CCCTTTCGTC

TTCAA
```

FIG. 24N

CKS METHOD OF HCV PROTEIN SYNTHESIS

BACKGROUND OF THE INVENTION

This application is a continuation-in-part of U.S. Pat. application Ser. No. 07/573,103, filed Aug. 24, 1990 now abandoned, which is a continuation of U.S. Patent application Ser. No. 07/276,263, filed Nov. 23, 1988, now U.S. Pat. No. 5,124,255, which is a continuation-in-part of U.S. patent application Ser. No. 07/167,067, filed Mar. 11, 1988 now abandoned.

This invention relates to methods for producing proteins in microbial hosts, particularly hepatitis core virus (HCV) fusion proteins. The invention also relates to cloning vehicles for transformation of microbial hosts.

It is well established that prokaryotic or eukaryotic proteins can be expressed in microbial hosts where such proteins are not normally present in such hosts (i.e. are "heterologous" to the cells). Generally, such protein expression is accomplished by inserting the DNA sequence which codes for the protein of interest downstream from a control region (e.g. a lac operon) in plasmid DNA, which plasmid is inserted into the cell to "transform" the cell so it can produce (or "express") the protein of interest.

Despite this conceptually straightforward procedure, there are a number of obstacles in getting a cell to synthesize a heterologous protein and subsequently, to detect and recover the protein. The heterologous gene may not be efficiently transcribed into messenger RNA (mRNA). The mRNA may be unstable and degrade prior to translation into the protein. The ribosome binding site (RBS) present on the mRNA may only poorly initiate translation. The heterologous protein produced may be unstable in the cell or it may be toxic to the cell. If no antibodies to the protein are available or if there is no other way to assay for the protein it may be difficult to detect the synthesized protein. Lastly, even if the protein is produced, it may be difficult to purify.

Fusion systems provide a means of solving many of the aforementioned problems. The "carrier" portion of the hybrid gene, typically found on the 5' end of the gene, provides the regulatory regions for transcription and translation as well as providing the genetic code for a peptide which facilitates detection (Shuman, et al., *J. Biol. Chem.* 255, 168 (1980)) and/or purification (Moks, et al., *Bio/Technology* 5, 379 (1987)). Frequently, potential proteolytic cleavage sites are engineered into the fusion protein to allow for the removal of the homologous peptide portion (de Geus, et al., *Nucleic Acids Res.* 15, 3743 (1987); Nambiar, et al., *Eur. J. Biochem.* 163, 67 (1987); Imai, et. al., *J. Biochem.* 100, 425 (1986)).

When selecting a carrier gene for a fusion system, in addition to detectability and ease of purification, it would be extremely advantageous to start with a highly expressed gene. Expression is the result of not only efficient transcription and translation but also protein stability and benignity (the protein must not harm or inhibit the cell host).

SUMMARY OF THE INVENTION

This invention is a process for making proteins, particularly HCV proteins, where a fusion protein of an *E. coli* enzyme, CKS (CTP:CMP-3-deoxy-D-mannooctulosonate cytidylyl, transferase or CMP-KDO synthetase), and a heterologous protein, such as heterologous HCV protein, is expressed in cells transformed with a cloning vehicle which has a DNA insert coding for CKS and the heterologous protein. The level of expression of CKS fusion proteins in cells transformed with such cloning vehicles is quite high, in some instances up to 50 percent of total cellular protein.

BRIEF DESCRIPTION OF THE DRAWINGS

FIG. 5 is a Coomassie brilliant blue-stained gel of various amounts of whole cell lysate from pTB201-containing JM103 cells. A corresponding gel scan/integration is also shown.

FIG. 9 (parts 1, 2 and 3) is a sequence of the synthetic p41 full-length gene with the carboxy terminus of p120. The broken line over the sequence indicates the sequence of pTB310B. The sequence of pTB310A is the same as pTB310B except for the deletion of an A (nt 813) indicated by Δ. Plasmid pTB321 includes Insert 1 (nt 15–143) which encode the carboxy terminus of p120. Plasmid pTB322 contains Insert 2 (nt 610–720) which encodes the hydrophobic region of p41.

FIG. 14 presents the DNA and amino acid sequences of the synthetic HIV-2 TMP fragment including Hind III/B g l II linker sequences located 5' and a Sal I linker sequence located 3' to the HIV-2 TMP fragment.

FIG. 18 (Parts A-J) represents the DNA sequence of pJ0200 and the amino acid sequence of pHCV-34.

FIG. 24 (Parts A-N) represents the DNA sequence of pHCV-31 and the amino acid sequence of HCV CKS-33-BCD.

DETAILED DESCRIPTION

1. General

Figure 1:
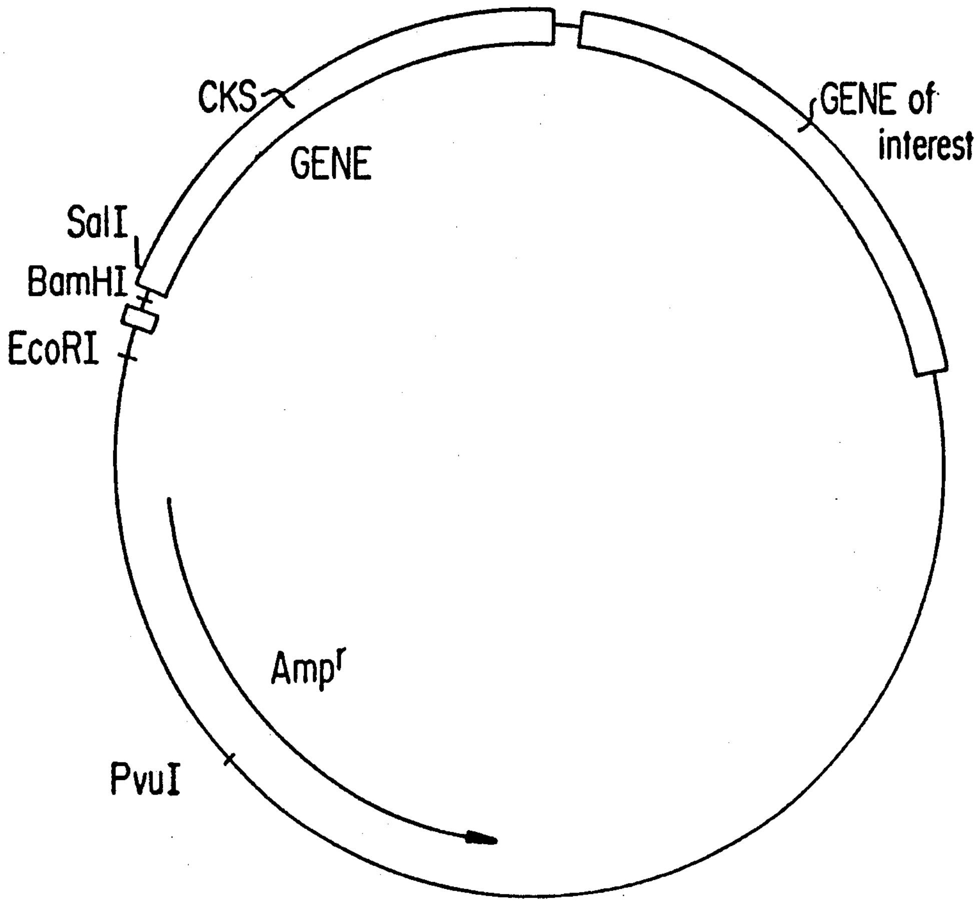
FIG. 1 is a graphic representation of a plasmid cloning vehicle of the present invention.

This invention involves the expression of a gene coding for a protein of interest, particularly HCV protein, using a DNA cloning vehicle which includes a control region, a region coding for the bacterial enzyme CKS (CMP-KDO synthetase), and a region coding for the protein of interest. The cloning vehicles of this invention are capable of expressing fusion proteins (i.e. CKS-heterologous protein fusions) at high levels. The invention is illustrated in FIG. 1 which shows generically the features of a plasmid of this invention. The plasmid of this invention includes a control region (e.g. a lac-type promoter with a sequence for a synthetic ribosome binding site), followed by a gene encoding CKS, which is linked to a gene coding for a heterologous protein of interest.

While fusion proteins per se are well established in the art, the use of CKS as a fusion system is novel. In addition to facilitating detection and purification of heterologous proteins, the expression vector of this invention utilizes the kdsB gene (encoding CKS) which, with the appropriate control region, expresses at higher levels than any other gene in *E. coli* in our hands.

2. Control Region

Figure 4:
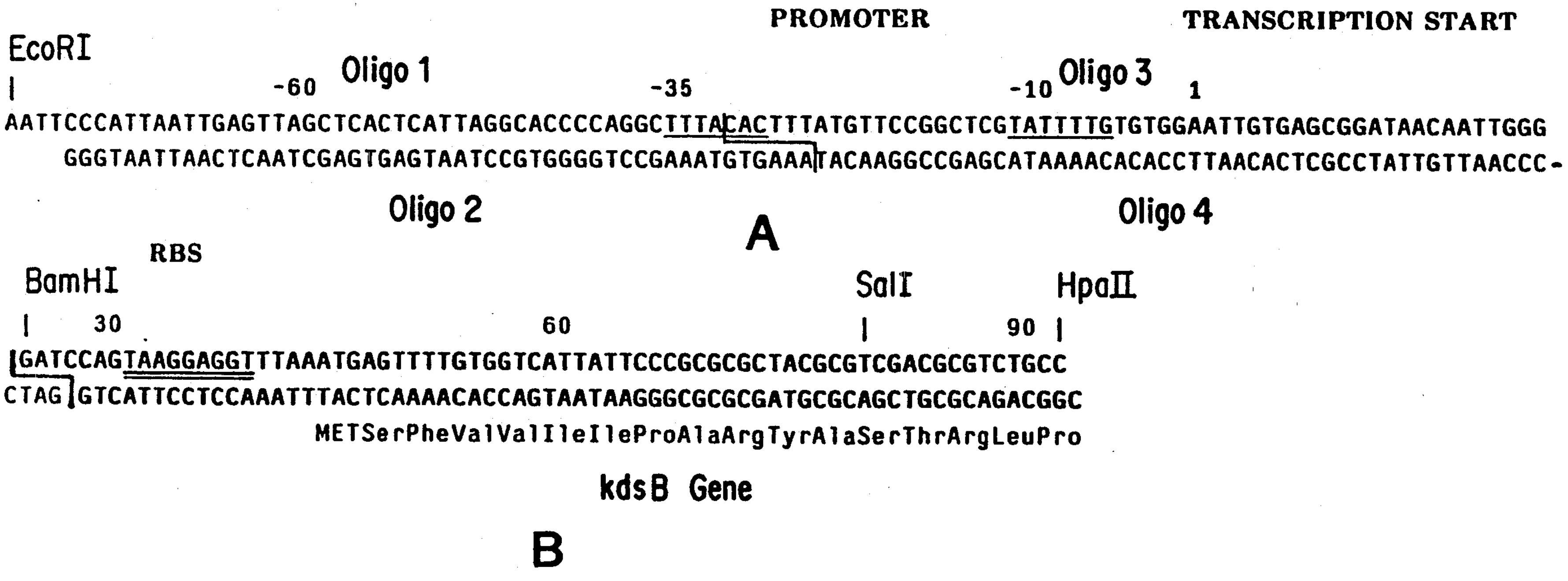
FIG. 4 is the DNA sequence for a synthetic lacP-type promoter used in the cloning vehicles of the present invention.

The control region of this invention is shown in FIG. 4. It includes a modified lac promoter which is essentially native lacP from −73 to +21 with two modifications: 1) a deletion at −24 of one G/C base pair, and 2) a T→A substitution at the −9 position. The control region also includes a synthetic ribosome binding site (nt 31-39) which is homologous to the 3' end of the 16S rRNA (ribosomal ribonucleic acid) in *E. coli.* Following the ribosome binding site is a consensus spacer region which is followed by the ATG translation initiation codon, followed by the structural gene for CKS.

3. CKS Structural Gene

The sequence for the structural gene encoding CKS (the kdsB gene) is published in Goldman et al., *J. Biol. Chem.* 261:15831, 1986. The amino acid sequence for CKS derived from the DNA sequence is described in the same article.

Figure 3:
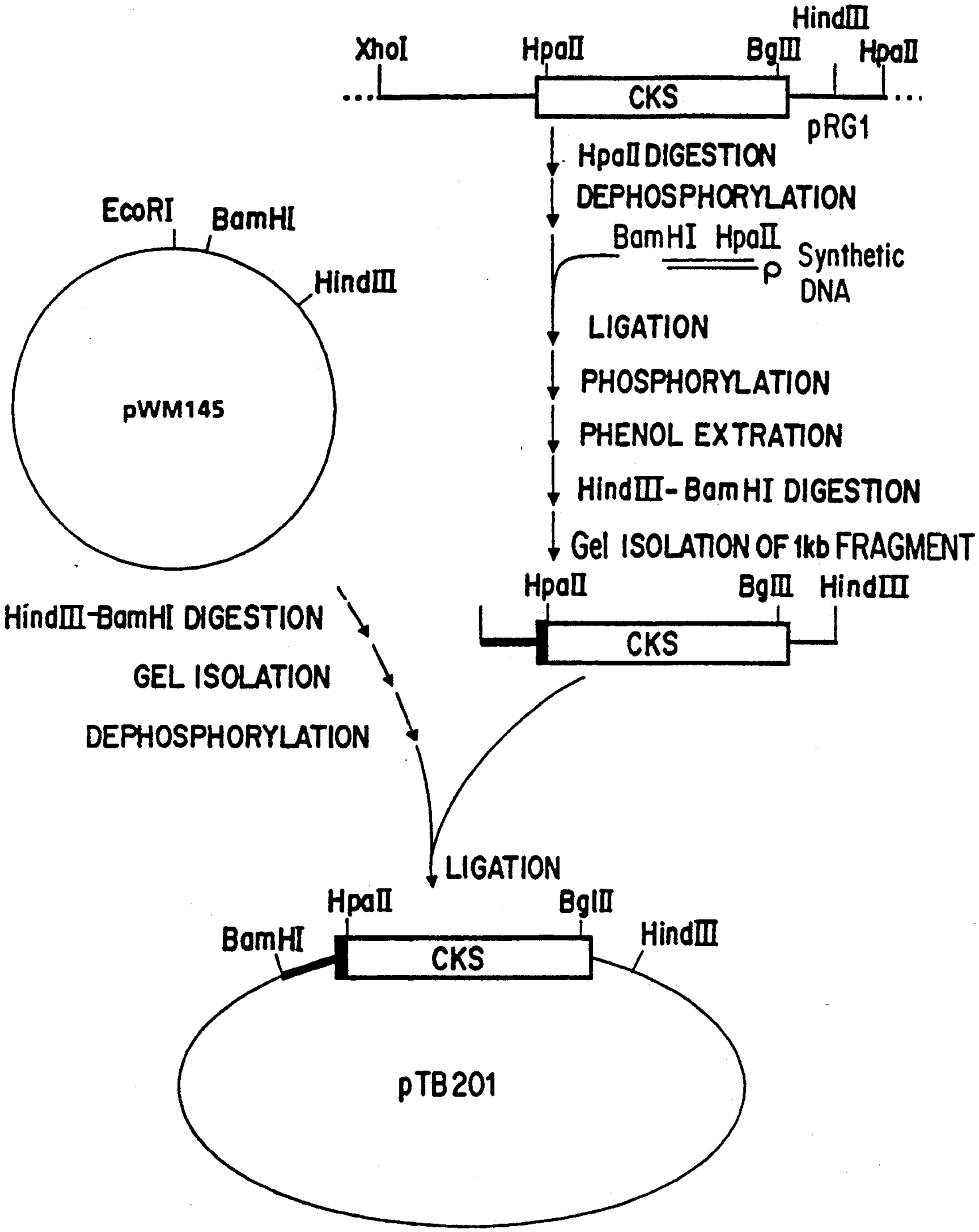
FIG. 3 is a schematic representation of the construction of pTB201 from pWM145.

The kdsB gene was obtained from Goldman's plasmid pRG1 (*J. Bacteriol.* 163:256) (FIG. 3). The first step in the kdsB gene isolation was a HpaII digestion of pRG1. Digestion with HpaII cleaved 51 base pairs from the 5' end of the gene.

A DNA fragment including the base pairs from the BamHI site to the HPaII site of FIG. 4 was constructed by annealing synthetic oligonucleotides (Example 1). This DNA sequence included the ribosome binding site as well as the 51 base pairs for the 5' end of the kdsB gene. The BamHI-HpaII fragment was then ligated to the HpaII native kdsB gene containing fragment, as described in detail in Example 1. As can be seen, the ligation replaced the 51 base pairs lost to kdsB, and added the ribosome binding site for the control region.

4. Construction of CKS Expression Vector

Figure 2:
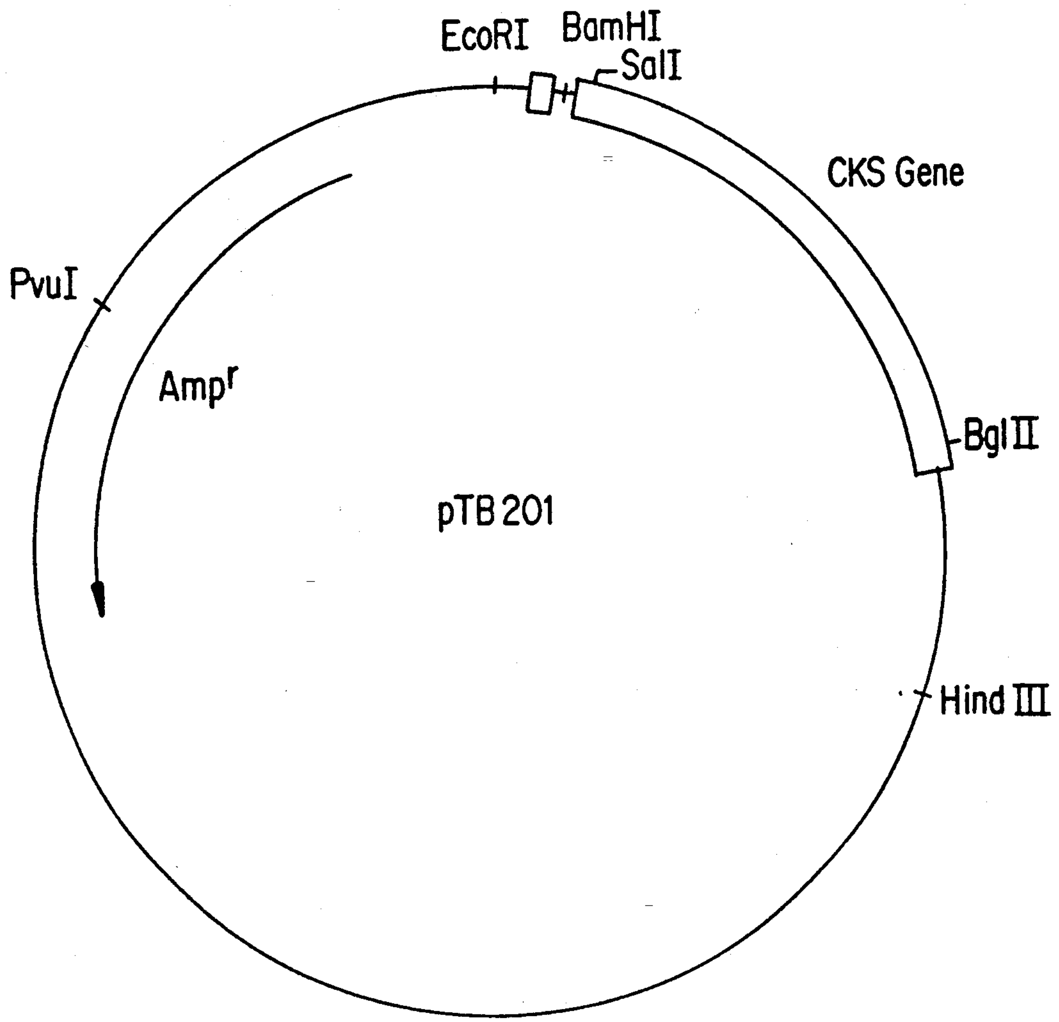
FIG. 2 is a graphic representation of a plasmid pTB201 containing a gene for CKS.

The pWM145 plasmid containing the modified lac promoter located between the EcoRI and BamHI sites shown in FIG. 4A was digested with BamHI and HindIII to provide an insertion site for the BamHI-HindIII fragment containing the CKS structural gene (FIG. 3). The kdsB containing fragment was then ligated into the pWM145 vector, assembling the control region containing the modified lac promoter and the ribosome binding site in the process. This produced plasmid pTB201 (FIGS. 2 and 3).

Figure 7:
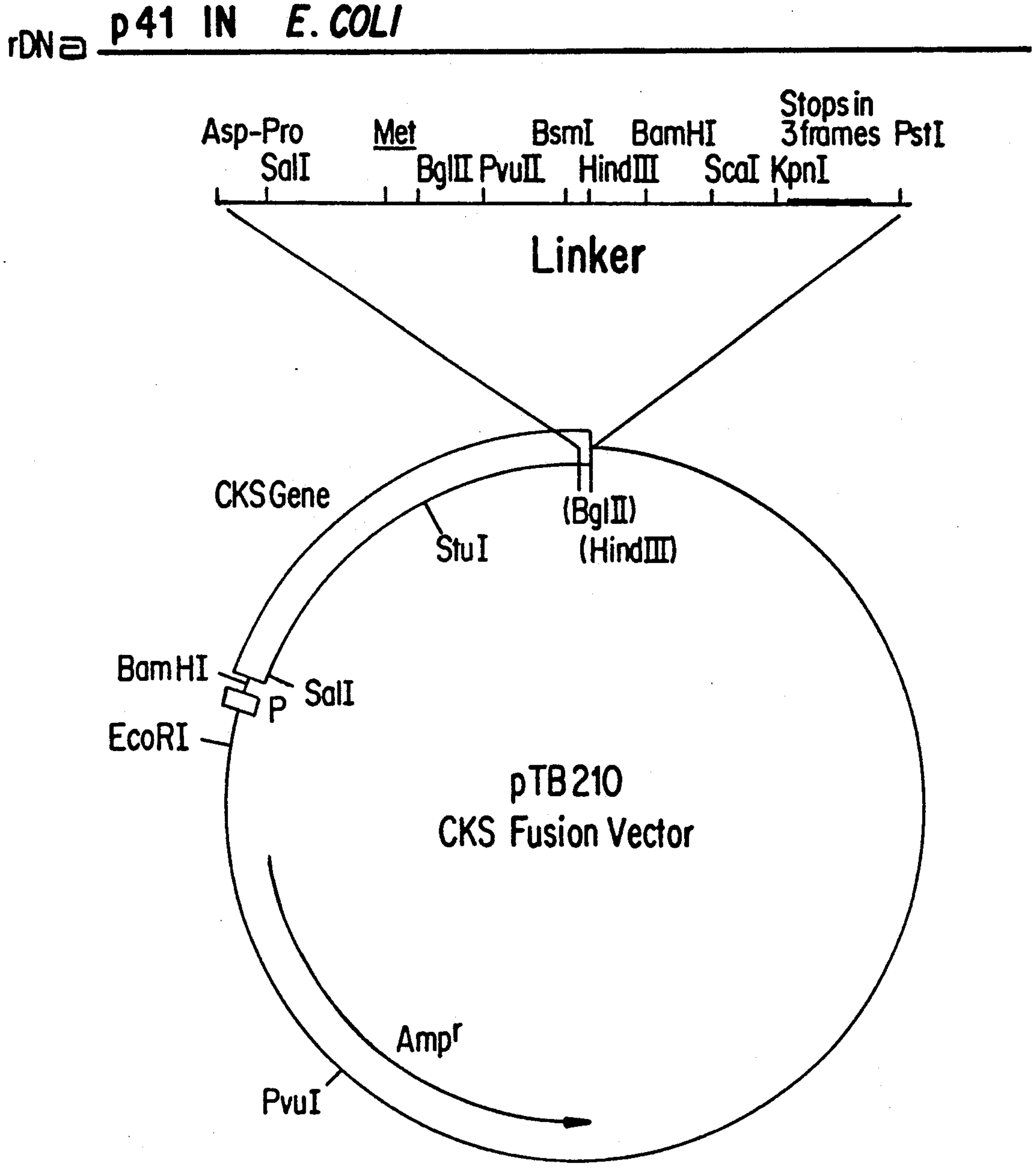
FIG. 7 is a graphic representation of a plasmid, pTB210, used to express HIV p41 fusion proteins.

5. Insertion of Linker Allowing Cloning of Heterologous Genes pTB201 is a fusion expression vector for heterologous genes which have the appropriate reading frame when cloned into the BglII or the BglII-HindIII sites (FIG. 2). However, the versatility of pTB201 can be improved by introducing other restriction endonuclease cloning sites. This is shown in FIG. 7 where a linker containing multiple restriction sites replaces the BglII-HindIII fragment of pTB201 to produce a new vector, pTB210. The linker also includes a sequence coding for Asp-Pro which allows for cleavage of the CKS protein from the heterologous protein fused to it.

The linker of FIG. 7 also includes stop codons in all three reading frames, placed downstream of the restriction sites. Thus, no matter what heterologous structural gene or portion thereof is inserted in the linker, translation will terminate immediately after the inserted gene.

6. Insertion of Heterologous Genes into pTB210

Insertion of heterologous genes into a plasmid of this invention can be accomplished with various techniques, including the techniques disclosed in U.S. patent application Ser. No. 883,242 entitled "Method for Mutagenesis By Oligonucleotide-Directed Repair of a Strand Break", filed Jul. 8, 1986, in U.S. patent application Ser. No. 131,973 entitled "FoKI Method of Gene Synthesis", filed Dec. 11, 1987, and in U.S. patent application Ser. No. 132,089 entitled "Method for Mutagenesis by Oligonucleotide-Directed Repair of a Strand Break", filed Dec. 11, 1987, all of which are incorporated herein by reference.

7. Examples

The present invention will now be illustrated by the following Examples. Example 1 describes the construction of a plasmid pTB201 which contains a modified lac promoter and the kdsB gene. In Example 2, cells containing pTB201 are used to express the CKS protein to establish that the kdsB gene is functional. In Example 3, goat anti-CKS sera is raised to detect the fusion proteins such as the one produced in Example 4. In Example 4, a fusion protein of CKS and HIVI p41 is disclosed. In Example 5, fusion proteins of CKS and various permutations of synthetic HIVI p41 and p120 are disclosed. In Example 6, a fusion protein of CKS and HSVII gG2 is disclosed. In Example 7, a fusion protein of CKS and the "kringle" region of tPA (tissue-plasminogen-activator) prepared. In example 8, two fusion proteins of CKS and SPL (pVAI) are prepared. In Example 9, a fusion for CKS and SPL(phe) is prepared. In Example 10, a fusion for CKS and HIV-2 is prepared. I Example 11 and 12, a fusion for CKS and HCV is prepared.

Example 1

CKS Expression Vector

A. Construction and Preparation of pWM145

The plasmid. pWml45, is a derivative of the C5a expression vector, pWmIII. (Mandecki, et al., Gene 43:131, 1986) Whereas the pWMIII vector contains a lacP-UV5-D24 promoter, the pWM145 vector contains a lacP-T9-D24 promoter. The changes were accomplished by replacing the promoter/operator region of pWMlll contained within a EcoRI-BamHI fragment with a synthetic fragment (FIG. 4A) containing the modifications. The following procedure was used.

Plasmid DNA (pWMlll) was isolated from JM83 (ara, (lac-proAB), rpsL, o80, lacZ M15) cells using a standard alkaline extraction protocol followed by purification on a cesium chloride gradient and precipitated with three volumes of 70% ethanol at −20° C. for two hours followed by centrifugation. DNA was resuspended in distilled water to a concentration of 1 mg/mL.

One microgram of pWMlll DNA was digested for two hours concomitantly with ten units of EcoRI and ten units of BamHI in 20 μL of a buffer consisting of 50 mM Trus, pH 7.5;10 mM $MgCl_2$; and 100 mM NaCl. Following digestion, the three kilobase plasmid was purified by 5% (50:1 acrylamide:BIS) polyacrylamide gel electrophoresis (PAGE). The fragment was cut out and extracted by shaking overnight at 37° C. in 10 volumes of 500 mM ammonium acetate, 10 mM magnesium acetate, 1 mM EDTA, and 0.1% SDS. The SDA was precipitated by chilling it for two hours at −20° C. with 2.5 volumes of 100% ethanol, followed by centrifugation.

The EcoRI-BamHI promoter fragment was composed of four oligonucleotides (oligos 1 through 4 indicated by brackets in FIG. 4A) which were purified by 20% PAGE under denaturing conditions and annealed by mixing equal molar amount of the oligonucleotides together in ligation buffer (66 mM Tris, pH 7.6; 6.6 mM $MgCl_2$; 50 μg/mL BSA; 10 mM dithiothreitol; 1 mM ATP), maintaining the mixture at 80° C. for five minutes, cooling the mixture slowly to 25° C., the refrigerating for one hour. A ten fold molar excess of annealedoligonucleotides was ligated together with approximately 50 ng of the purified EcoRI-BamHI digested vector and one unit T4 ligase in 20 μL volume ligase buffer at 16° C. overnight. One-forth of the ligation mix was used to transform competent JUM103, (supE, thi, (lac-proAB), endA, rpsL, sbcBl5[F', traD36, proAB, lacIq Z Ml5] using standard protocol (Madel & Higa, *J. Mol. Biol*, 53:154, 1970). Plasmid DNA from the transformants was prepared from 150 mL cultures as described above, and the DNA was sequenced using Sanger methodology (*Pro. natl. Acd. Sci.* USA 24:5463, 1977).

B. Construction and Preparation of pTB201

The kdsB gene from *E. coil* K-12, which encodes CTP:CMP-3-dexoy-D-manno octulosonate cytidylyltransferase (CMP-KDO synthetase), was isolated from pRGl. The gene is almost entirely contained within a HpaII fragment (FIG. 3). A linker was constructed to facilitate cloning kdsB into pWMl45. The linker not only provided a BamHI site for subsequent cloning but also included a strong ribosome binding site, and the DNA sequence coding for 17 amino acids at the amino terminus of CKS (FIG. 4B). The procedure for construction, shown in FIG. 3, was as follows:

1a. Plasmid pRGl was digested with HpaII and dephosphorylated with bacterial alkaline phosphate (BRL). The 1.7 kbsB gene fragment was isolated on a 5% (50:1) Acrylamide:BIS gel, eluted, and purified as described above.

1b. Oligonucleotides (shown in FIG. 4B) were synthesized, purified , labeled (using BRL T4 Kinase, with a 2X molar excess of ATP [1 part gamma [$^{32}$P]ATP to 9 parts nonradioactive ATP] and BRL recommended protocol) and annealed.

2. Ligation of HpaII gene fragment with the synthetic fragment was carried out at 16° C. overnight. Ligase was heat inactived (15 min at 65° C.). DNA was then phosphorylated (as above), phenol extracted (1X 1 vol buffer equilibrated phenol, 1X 1 vol chloroform:isoamyl alcohol), ethanol precipitated, and resuspended in medium salt buffer (50 mM Tris, pH 7.5, 10 nMM, $Cl_2$, and 50 mM NaCl). Following simultaneous digestion with HIndIII and BamHI, the DNA was purified from a 50% (50:1) acrylamide gel.

3. The pWMl45 vector was digested with HindIII and BamHI, dephosphorylated, and purified from a 50% (50:1) acrylamide gel as above. The vector (15 ng) and insert (20 ng) were ligated overnight at 16° C. One-half of the total ligation mix was used to transform competent J103 cells. The pTB201 construct was varied by DNA sequencing.

Example 2

Expression of kdsB Gene and Purification of CKS From TB201/JM103 Cells

Cultivation of pTB201/JMl03 cells

A 50 mL flask containing 10 mL LB broth with 50 μg/mL ampicillin was inoculated with a loopful of frozen stock pTB201/JMl03 cells. The culture was incubated at 37° C. while shaking at 225 RPM. When the culture became turbid, the 10 mL were used to inoculate one liter of LB/Amp in a four liter flask. At an $OD_{600}=0.3$; IPTG (isopropyl-thio-ƒ-galactoside) was added to a final concentration of 1 mM, and the cells were incubated overnight. A typical SDS-PAGE of the whole cell lysate as well as gel scan on the sample is shown in FIG. 5. The relative percentage of the CKS to the total cellular proteins is 50 to 75%.

B. Purification of CKS

Purification procedure was that described by Goldman and Kohlbrenner (*J. Bacteriol.* 163; 256–261) with some modifications. Cells were pelleted by centrifugation, resuspended in 50 mM potassium phosphate (pH 7.6), and lysed by two passages through a French Press (15,000 PSI). The lysate was spun at 30,000×g for 30 minutes. The soluble fraction was treated with protamine sulfate and ammonium sulfate, and dialyzed as described (Ray, et al., *Methods Enzymol.* 83:535 1982). The sample was passed for final purification through a BioRad DEAE-5 PW HPLC-ion exchange column and eluted with a 50–400 mM potassium phosphate (10% acetylnitrile) gradient.

Example 3

Generation of Goat Anti-CKS Sera

A. Goat immunization and bleeding

A goat was immunized monthly in three general areas inguinal (subcutaneously), auxiliary (subcutaneously) and hind leg muscles. Initial inoculation consisted of 1 mg purified CKS in complete Freund's Adjuvant. Thereafter, the boosting inoculum consisted of 0.5 mg purified CKS in incomplete Freund's Adjuvant. Five-hundred milliliters of blood was collected from the goat two and three weeks post-inoculation starting after the second boost. The blood was allowed to clot overnight, and the serum was decanted and spun at 2500 RPM for thirty minutes to remove residual red blood cells.

B. Immunoblotting

Figure 6:
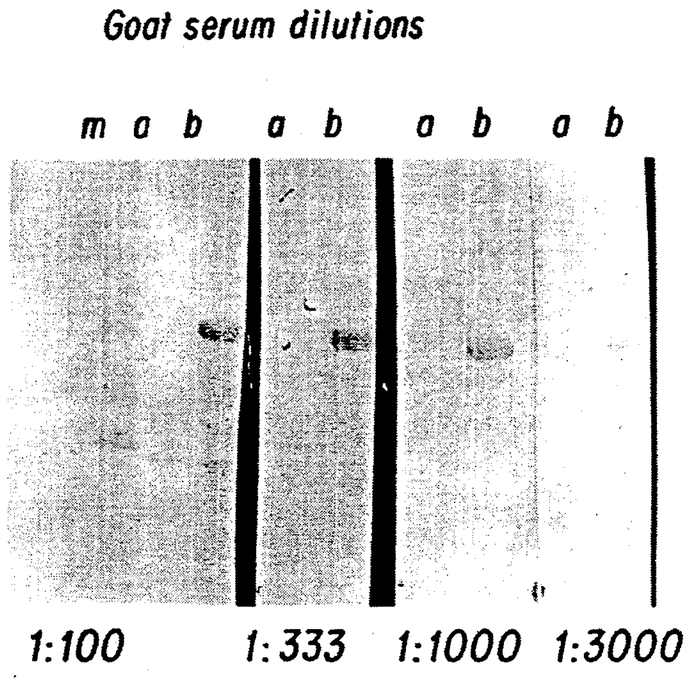
FIG. 6 shows immunoblots of CKS-producing and nonproducing cells used to optimize the titration of goat anti-CKS serum for identifying CKS fusion proteins. M is protein molecular weight markers; A, negative control JM103 whole cell lysate; B, positive control pTB201/JM103 whole cell lysate.

The presence of anti-CKS antibodies in the goat serum was confirmed by immunoblotting (FIG. 6). Whole cell lysates of pTB201/JM103 (labeled "b" in FIG. 6) and JM103 (labeled "a") controls were run on a 12.5% SDS-polyacrylamide gel, and proteins were electrophoretically transferred (Towbin, et al., *Proc. Natl. Acad. Sci.* USA 76:4350) to nitrocellulose. The filter was cut into strips which were pre-blocked with immunoblot buffer (5% instant dry milk, 1×TBS [50 mM Tris, pH 8.1; 150 mM NaCl], 0.01% Antifoam C Emulsion) for fifteen minutes with agitation. Strips were placed into separate containers with immunoblot buffer and various amounts of serum (from 1:100 to 1:3000) were added. After one and one-half hours of agitation, the buffer was poured off, and the strips were washed three times for five minutes with 1×TBS. The second antibody, horseradish peroxidase-labeled rabbit anti-goat (BioRad), was added to the strips at a 1:1500 dilution in immunoblot buffer. Following one and one-half hours of agitation, the buffer was poured off, and the strips were washed as above. Blots were developed for 5–10 minutes with agitation after addition of the developing agent (0.5 mg/mL of 3,3'-diaminobenzidine tetrahydrochloride dihydrate, 0.1 μg/mL of $H_2O_2$ in 1×TBS). A 1:3000 dilution of the serum was optimal, giving strong positive bands and negligible background.

EXAMPLE 4

Fusion protein—CKS/HIVI p41 HaeIII-HindIII

As an example of expression of a hydrid gene, a portion of the HIVI (human immunodeficiency virus I) p41 (envelope) gene was cloned into the CKS expression vector. The resulting gene coded for a protein fusion which consisted of CKS (less nine residues at the carboxy terminus), a nine amino acid residue linker, and a major epitope of the HIVI virus (amino acid positions 548–646 based on the precursor envelope protein, p160, numbering by Ratner, et al., Nature 313:227, 1985) (refer to FIG. 8). In order to assure the proper reading frame of the HIVI portion of the gene, a linker was designed and cloned into the pTB201 plasmid. The linker and HIVI gene fragments were cloned as close to the distal end of the kdsB gene as conveniently possible. Our rationale was that maximizing the amount of kdsB gene would maximize the chance of success for high level expression of the heterologous gene.

A. Construction of pTB210

The pTB210 plasmid (FIG. 7) was a derivative of the pTB201 plasmid (described above). pTB201 was digested with BglII and HindIII, and the 3.6 kb vector fragment was purified from a 5% (50:1) acrylamide gel. The linker, composed of two synthetic oligonucleotides with overhangs compatible with BglII and HindIII ends, was ligated into the vector, and the ligation mixture was used to transform competent JM109 cells (recA1, endA96, thi, hsdR17, supE44, relA1, λ-, (lac-proAB), [F', traD36, proAB, lac IqZ M15]). DNA sequencing was used to confirm the construction.

B. Construction of pTB211

The pTB211 plasmid was the vector construction used to express the hybrid kdsB-HIVI p41 major epitope gene. The source of HIVI DNA was a plasmid which contained the p160 gene of HIVI (HTLVIIIB isolate from NIH) cloned as a KpnI fragment into pUC18. The plasmid was digested with HaeIII and HindIII and a 296 bp fragment was isolated from a 5% acrylamide gel. This fragment was ligated into PvuII-HindIII digested pTB210 vector followed by transformation into competent JM109 cells.

C. Screening of Transformants

The transformed cells were plated on LB/AMP plates. Following overnight incubation at 37° C., several colonies were picked from the plate and used to inoculate 2 mL of LB/Amp broth. Cultures were grown to an $OD_{600}$ of 0.3–0.5 then IPTG was added to a final concentration of 1 mM. Cultures were shaken at 37° C. for an additional three hours. The absorbance of the cultures at 600 nm was measured; cells from one milliliter of each culture were precipitated by centrifugation, and then resuspended to an $OD_{600}$ equivalent of ten in treatment buffer (63 mM Tris, pH 6.8, 2%SDS, 10% glycerol, 5% 2-mercaptoethanol). Following a 10 minute incubation in a boiling waterbath, an aliquot (10 μL) of each lysed culture was electrophoresed on 12.5% SDS-polyacrylamide gels. A protein band corresponding to the proper molecular weight of the fusion protein could be visualized directly on gels stained with Coommassie brilliant blue. Fusion protein could also be detected by immunoblots using the goat anti-CKS serum (method described in Example 3B.) and HIVI positive human serum (using human serum at 1:250 dilution and HRP conjugated goat anti-human antibodies at 1:1500). The fusion protein level in the cells after induction was 5–10% of the total cellular protein.

EXAMPLE 5

Fusion Protein—CKS/synthetic HIVI envelope peptides

In this example, hybrids of the kdsB and portions of a synthetic p41 genes expressed and produced fusion proteins to a level of up to 20% of the total cellular protein. Additionally, this example demonstrates the use of an Asp-Pro dipeptide in the linker region as a chemical cleavage site for cleaving the CKS portion of the protein from the HIVI portion. Further examples are included which demonstrate that multiple fusions (CKS peptide plus p41 and a portion of p120) were attainable. These are useful peptides for diagnostics.

A. Synthesis and cloning of the HIVI synp41d gene

Figure 8:
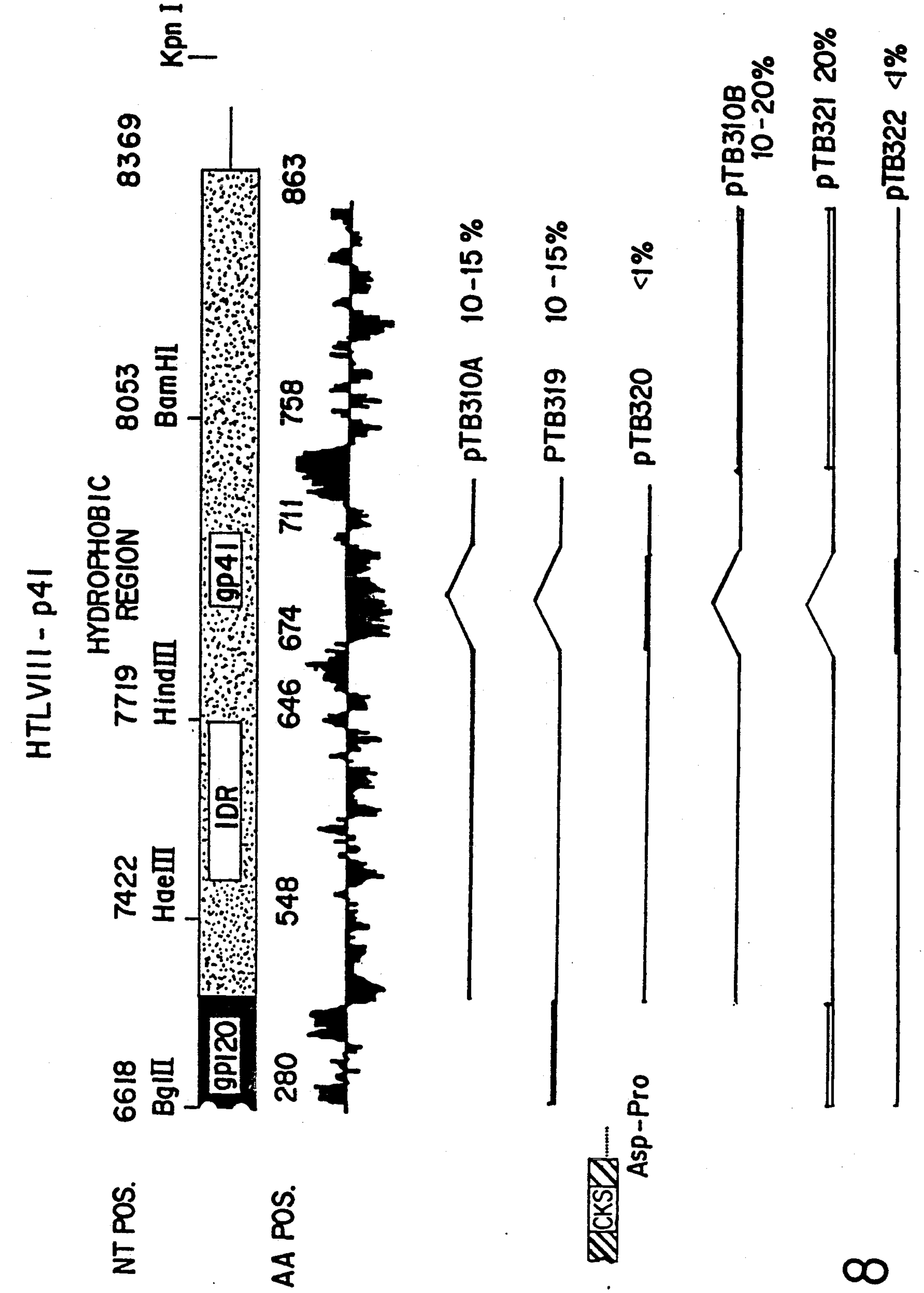
FIG. 8 shows a representation of the various synthetic p41 genes relative to the native gene. A hydrophobicity plot of the protein is also indicated. Levels of expression of each clone are included.

The synp41d gene codes for a deletion mutant of the HIVI p41 protein which contains a 38aa hydrophobic region deletion (from Ala674 to Val711 based on p160 numbering, refer to FIG. 8 plasmid, pTB310B). The gene was synthesized using the method of oligonucleotide directed double-stranded break repair as disclosed in U.S. patent application Ser. No. 883,242 filed Jul. 8, 1986, in U.S. patent application Ser. No. 131,973 filed Dec. 11, 1987, and in U.S. patent application Ser. No. 132,089 filed Dec. 11, 1987, all of which are incorporated herein by reference. The specific sequence is indicated by single-line overscore on FIG. 9. The synthetic gene contained flanking BamHI and KpnI sites to facilitate cloning into pTB210. The vector was digested with BglII and KpnI, and the BamHI-KpnI synthetic gene fragment was ligated into the vector. Following transformation into JM109 cells, clones were cultivated, induced, and screened for expression.

B. Characterization of fusion protein encoded by pTB310A

Upon the initial screening, a clone was discovered containing a plasmid (pTB310A) which had a A/T base deletion at nucleotide position 813 (based on FIG. 9 numbering). Although this mutation (which occurred in cloning the synthetic p41d gene) resulted in a truncation in the p41d portion of the fusion protein, the protein produced was characterized for its diagnostic potential.

Production and Purification

Ten mL of LB/Amp in a 100 mL flask was inoculated with 100 μL of an overnight pTB310A/JM109 culture. After shaking at 37° C. for one and one-half hours, IPTG was added to the culture to a concentration of 1 mM, and the cells were grown for four more hours. An aliquot (1 mL) of the culture was pelleted and lysed in an appropriate volume of 1× treatment buffer to give a final concentration of cells of 10 $OD_{600}$ absorbance units. This sample, referred to as WCL (whole cell lysate), was used to measure the amount of fusion protein relative to total cellular proteins. The remaining 9 mL of cell culture ws centrifuged (five minutes, 5000 rpm) and the cells were resuspended in 10 mM Tris (400 μL), pH 8.0, 1 mM EDTA with 2 mg/mL lysozyme. After fifteen minutes on ice, 10 μL of 20% Triton X-100 was added, and the cells were sonicated (6×30 sec). The lysate was spun in an Eppendorf centrifuge for five minutes. The supernatant was collected, and the pellet was resuspended in 8M urea (400 μL). The fusion protein present in the resuspended pellet fraction is about 75% pure based on Coommassie stained gels.

Western and Immunoblots

Figure 10:
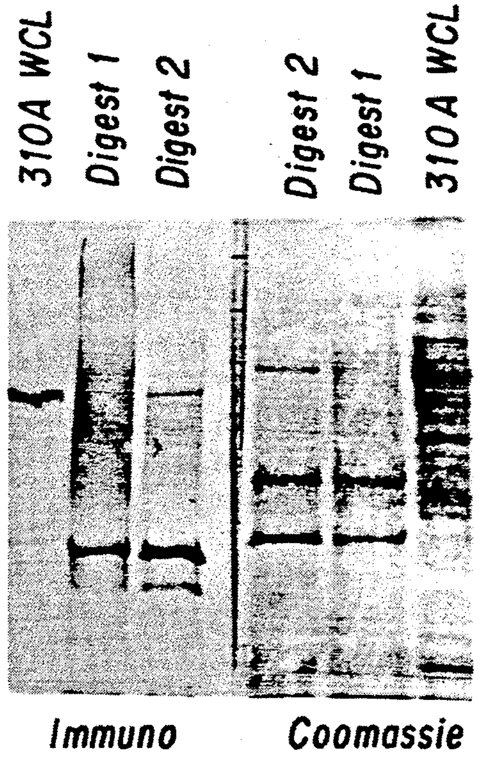
FIG. 10 illustrates the acid hydrolysate of the fusion protein expressed from pTB310. Coomassie brilliant blue-stained SDS-PAGE is pictured on the right. An immunoblot of an SDS-PAGE using human AIDS positive serum is shown on the left. Refer to text, Example 5B, for details.

A sample (10 μL) of pTB310A/JM109 WCL was loaded on a 0.7 mm thick 12.5% SDS-polyacrylamide gel, along with prestained protein molecular weight standards, WCL from JM109 without plasmid, and WCL from JM109 containing pTB210 (unfused CKS). Gel was run at 150 volts and terminated when bromophenol blue sample loading dye has reached the bottom of the gel. Proteins were then electrophoretically transferred to nitrocellulose. Immunoblotting was carried out as described in Example 3B. An example of pTB310A/JM109 WCL on a stained gel and immunoblot is shown in FIG. 10.

Chemical cleavage of fusion protein

An aliquot (30 μL) of the urea soluble fraction was diluted with ten volumes of water, and the insoluble fusion protein was pelleted by centrifugation. The protein was then dissolved in 30 μL of 6M guanidine hydrochloride, and 70 μL 98% formic acid added (Digestion 1). In a parallel experiment, 70 μL 98% formic acid was added to an aliquot (30 μL) of the urea fraction directly (Digestion 2). Following two days incubation at 42° C., ten volumes of water were added, and the insoluble proteins were pelleted by centrifugation. The pellet was resuspended in 1X treatment buffer (100 μL), and 10 μL was used per well on 12.5% SDS-polyacrylamide gel. FIG. 10 shows a sample of the cleaved products (Digestion 1 and Digestion 2) both on a Coommassie gel and an immunoblot (using HIVI positive human serum as primary antibody). Only two major bands are visible on the Coommassie gel. These represent the products of cleavage at the unique Asp-Pro bond: the CKS portion, MW=26.5 kDa and the p41 portion, MW=23.5 kDa. Peptide sequencing confirmed that the lower molecular weight band was indeed the p41 peptide, and that the amino terminal residue was proline which results from expected cleavage between the Asp and Pro.

C. Characterization of the pTB310B/JM109 clone

The clone containing the correct gene for the CKS-p41d fusion, pTB310B, was cultured and assayed for expression. The fusion protein represents 10–20% of the total cellular protein (dependent on growth and induction conditions).

D. Addition of the p120 carboxy terminal region

A synthetic DNA fragment which encoded the carboxy terminal 42 amino acids of HIVI p120 (Insert 1, FIG. 9) was inserted into the NarI site of pTB310A and pTB310B at nt 15. The resulting clones pTB319/JM109 and pTB321/JM109, respectively, expressed the triple fusion protein at levels of up to 20% total cellular protein.

EXAMPLE 6

Fusion protein-CKS/HSVII gG2

A 1.1 kb fragment containing the Herpes Simplex Virus II (HSVII) gG2 gene (encoding a major envelope glycoprotein) was isolated following digestion with AatII and XbaI. A synthetic linker was ligated to the XbaI end to generate an AatII end. Both ends were then made blunt by treating the 3' overhangs with T4 polymerase.

Figure 11:
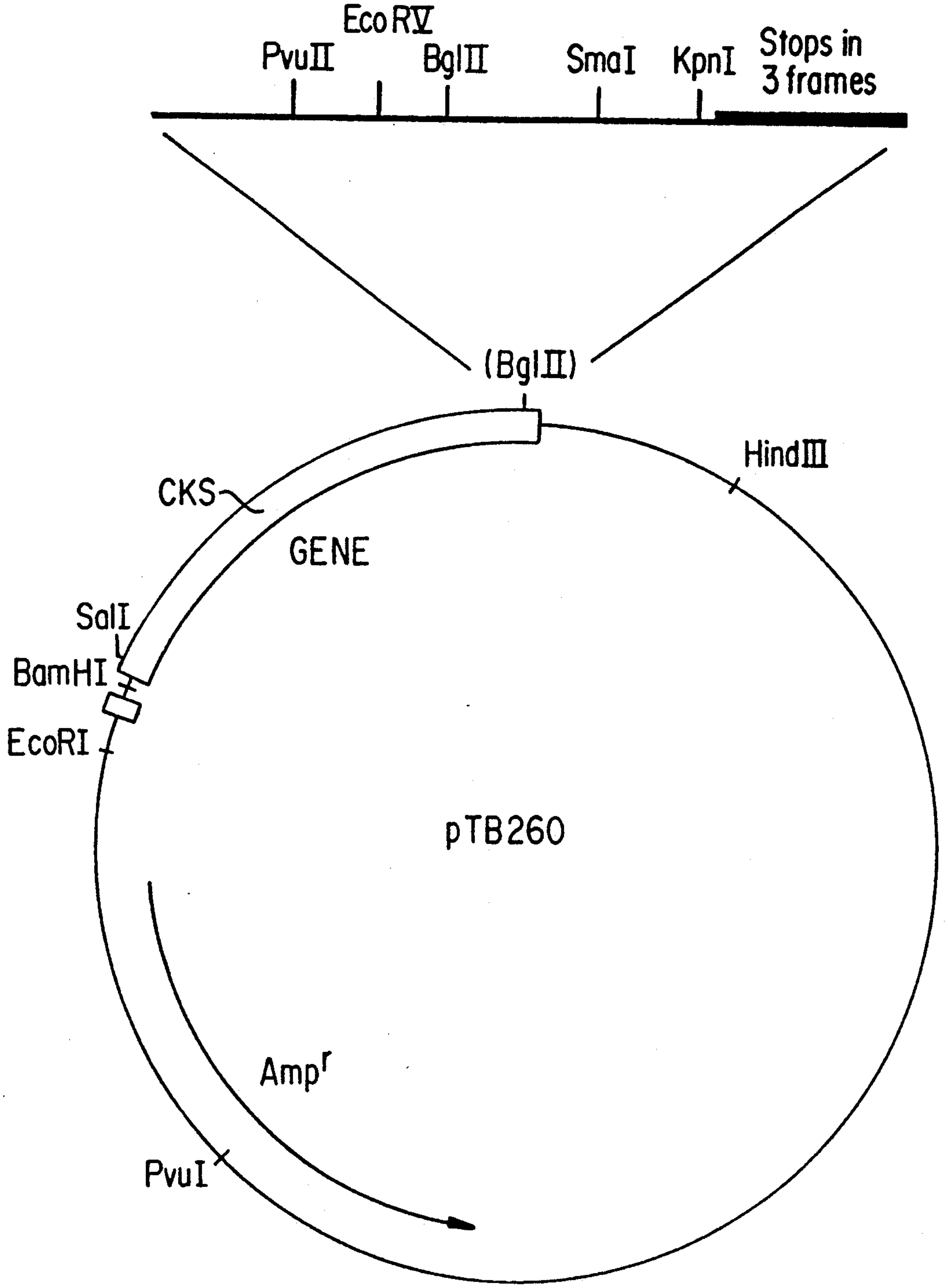
FIG. 11 is a graphic representation of a plasmid pTB260 used as a cloning vehicle of the present invention.

The vector in this example was pTB260 (FIG. 11). It was constructed by ligating a synthetic fragment with multiple restriction sites into the BglII site of pTB201. In cloning the fragment, the original BglII site from pTB201 was inactive and thus, the BglII site in the linker 8 fragment is unique.

To facilitate cloning the blunt-ended DNA fragment containing the gG2 gene and to put the gene in the proper reading frame of kdsB, the BglII digested pTB260 was made blunt-ended by filling in the overhangs using Klenow and dNTP's. Following ligation of the gG2 DNA with pTB260, the DNA was used to transform competent TB-1 cells. Whole cell lysate from transformants run on gels and immunoblotted with rabbit serum against HSVII proteins gave a visible band of the proper molecular weight.

EXAMPLE 7

Fusion protein-CKS/Kringle region of tPA

Figure 12:
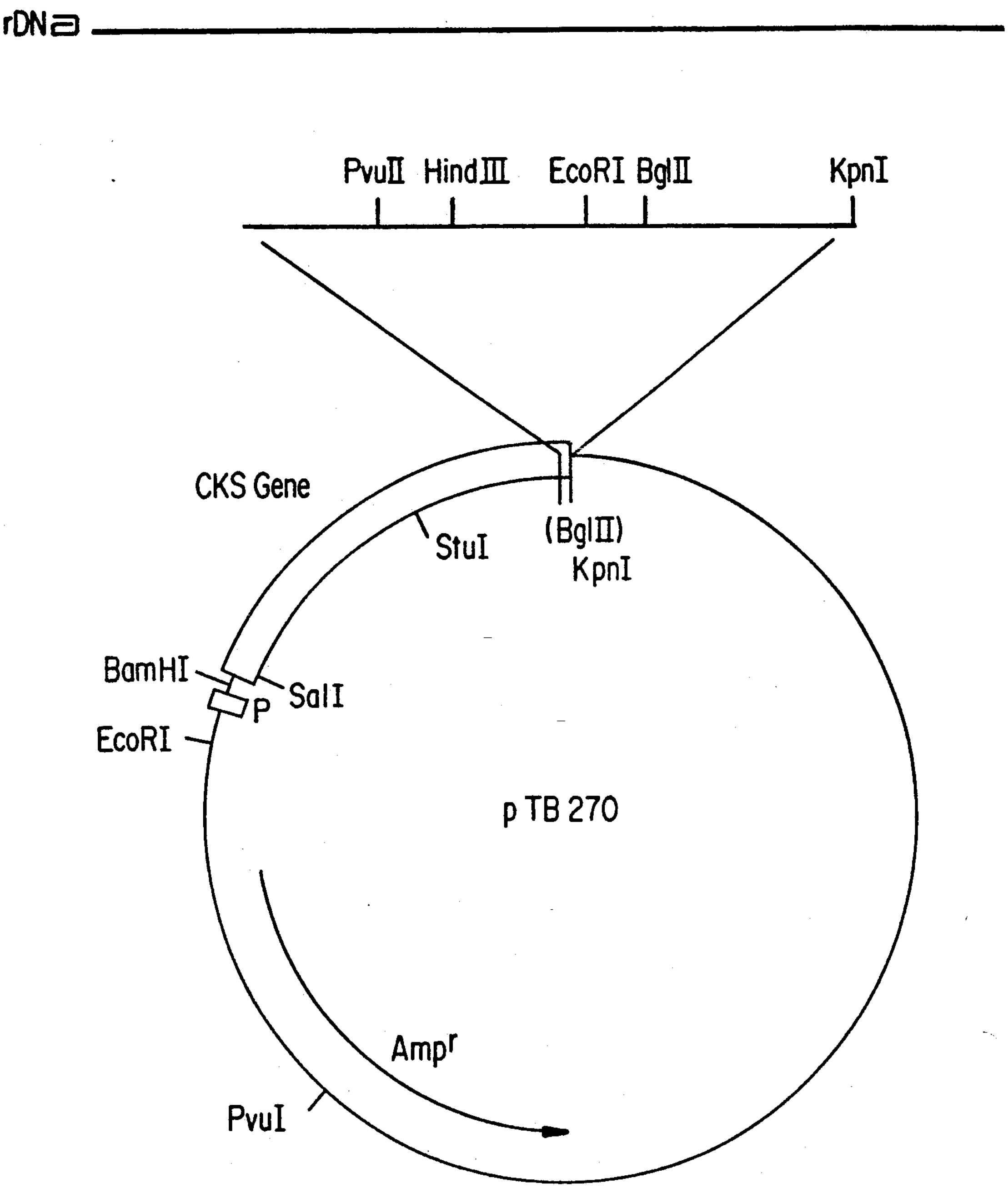
FIG. 12 is a graphic representation of a plasmid pTB270 used as a cloning vehicle of the present invention.

A gene coding for the "kringle" (Patthy, L., Cell, 41:657 (1985)) region of tissue-plasminogen-activator was synthesized and cloned as a 335bp HindIII-KpnI fragment into pTB270 (Zablen, L.B., unpublished). The pTB270 vector (FIG. 12) was a derivation of pTB210 which was constructed by ligatina synthetic multi-cloning site linker into BglII-KpnI digested pTB210. The pTB270 plasmid was then digested with HindIII-KpnI and ligated with the Kringle-region gene fragment. Transformation was carried in competent XL-1 Blue cells (Stratagene, La Jolla, Calif., USA). Clones containing the proper insert were confirmed by DNA sequencing of the plasmids. The level of the fusion protein reached 30%-40% of the total cellular proteins.

The CKS/Kringle protein was extracted from a culture by lysing the cells as in Example 5B, precipitating the cellular debris, and collecting the supernatant which contained the soluble fusion protein. Further purification was accomplished by "salting out" the protein. Briefly, ammonium sulfate was added to 10% (w/v), and the insoluble proteins were pelleted by centrifugation. The pellet of this fraction, after assaying to demonstrate the absence of fusion protein, was discarded. Ammonium sulfate was added to the supernatant to a final concentration of 30%, and the insoluble proteins were pelleted. This pellet contained 70% of the starting fusion protein amount and was 75% pure.

EXAMPLE 8

Fusion protein-CKS/SPL(PVal)

A. A human lung surfactant gene, SPL(pVal) (U.S. patent application Ser. No. 101,680, filed October 1987, contained within an 820bp EcoRI fragment was cloned into pTB210. The overhanging EcoRI ends were filled using Klenow and dNTP's. The blunt-ended fragment was then ligated into PvuII digested pTB210. Following transformation into competent XL-1 Blue cells (Stratagene, La Jolla, Calif., USA), DNA was isolated from a number of transformants and mapped with restriction endonucleases to identify clones with the insert in proper orientation. Expression level of the fusion protein based on whole cell lysates was 3%. The protein could be purified to about 50% purity by cell lysis and pelleting as described in Example 5B. The fusion protein was used to generate antibodies against the SPL peptide by immunizing rabbits with gel purified product.

Figure 13:
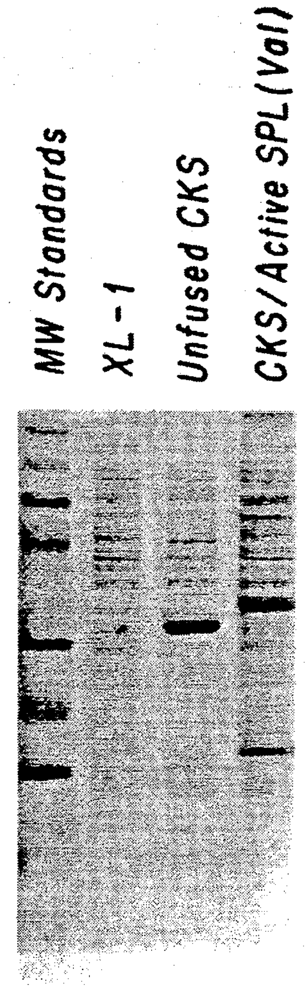
FIG. 13 is a Coomassie brilliant blue-stained SDS-PAGE gel. Approximately equal numbers of cells of each clone type were lysed and loaded on the gel. The lane marked "XL-1" is the cell lysate from the XL-1 Blue strain with no plasmid. "Unfused CKS" is lysate from XL-1 Blue cells containing the pTB201 CKS-expressing vector. "CKS/Active SPL (Val)" is lysate from an XL-1 cell line which contains the active region of the pVal lung surfactant gene in fusion with the kdsB gene on the pTB201 plasmid.

B. A hybrid gene containing kdsB with the 139 nt active region of pVal was constructed by cloning a BglII-HindIII-ended synthetic fragment encoding the active region (refer to patent) into BglII-HindIII digested pTB201. Assays of whole cell lysates indicated that expression levels of up to 40% of the total cellular protein were obtained (FIG. 13).

EXAMPLE 9

Fusion protein-CKS/SPL(phe)

A human lung surfactant gene, SPL(phe) (disclosed in U.S. patent application Ser. No. 101,680 described above), contained within a 1635bp EcoRI-HindIII fragment was cloned into pTB210. The gene was originally isolated from a clone, Phe 7-1, as a 1945 bp EcoRI fragment, blunt-end filled using Klenow and dNTP's, then digested with HindIII. This fragment was ligated into PvuII-HindIII digested pTB210 and transformed into competent XL-1 Blue cells. The CKS/SPL(phe) fusion protein level was 9% of the total cellular protein. The fusion protein was 50 pure in the pellet following lysis of the cells (procedure described in Example 5B). Gel purified CKS/SPL(Phe) was used to immunize rabbits to generate antibodies against the SPL(Phe) portion of the protein.

EXAMPLE 10

Fusion protein-CKS/synthetic HIV-2 TMP Fragment

In this example, a synthetic DNA fragment containing a portion of the HIV-2 (human immunodeficiency virus II) transmembrane protein (TMP) was cloned into the CKS expression vector. The resulting gene coded for a protein fusion consisting of CKS (less nine residues at the carboxy terminus), a ten amino acid residue linker, and the major epitope of the HIV-2 virus (envelope amino acid positions 502-609, numbering by Guyader, et al., Nature 326: 662, 1987) followed by another ten amino acid residue linker. This fusion protein was expressed to a level of up to 15% of the total cellular protein and proved useful in the detection of sera containing HIV-2 antibodies.

A. Synthesis and cloning of the HIV-2 TMP fragment

Figure 15:
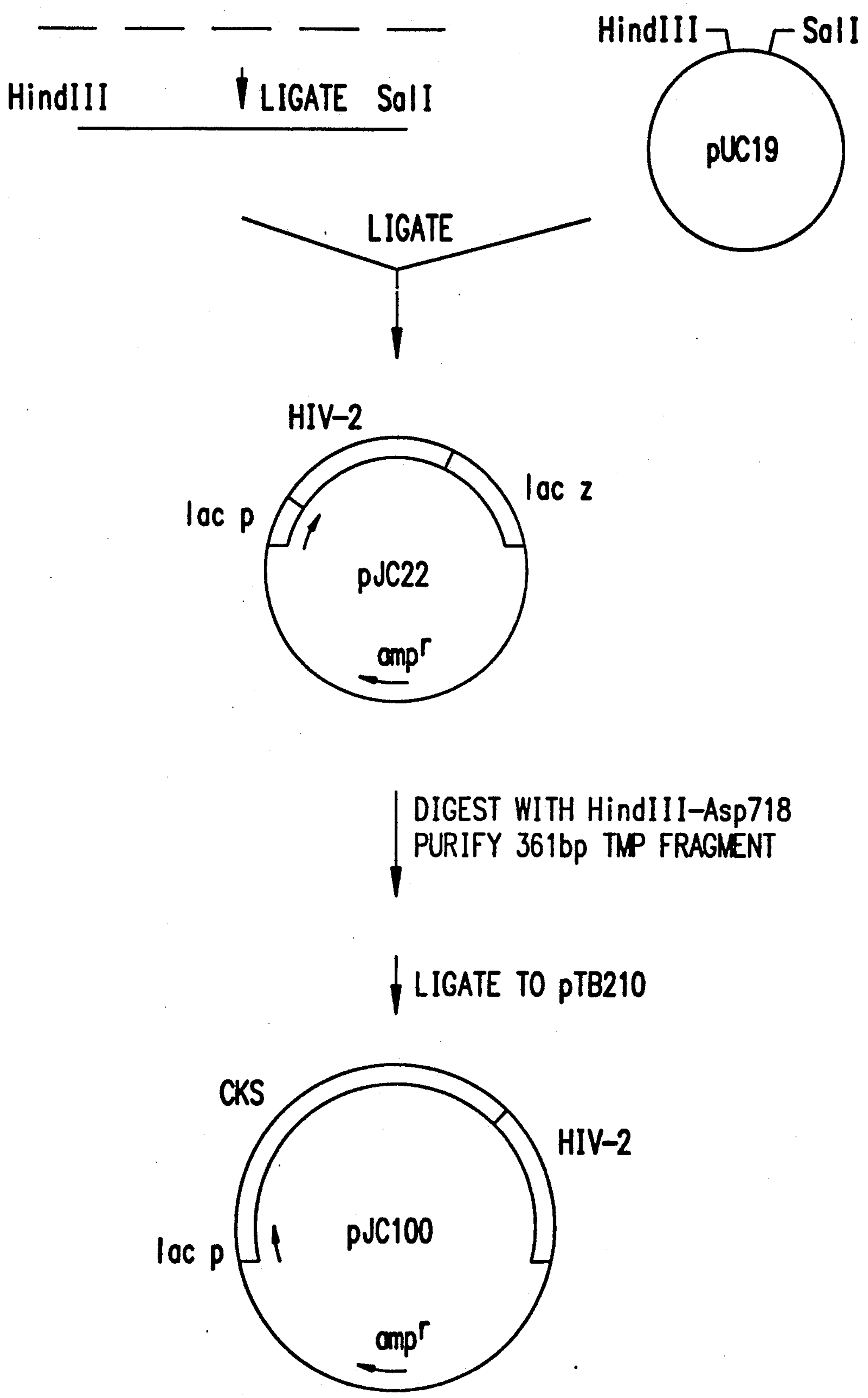
FIG. 15 is a schematic representation of the construction of pJC22 and pJC100.

The HIV-2 TP fragment codes for the amino terminal 108 amino acids of the HIV-2 TMP (from Tyr 502 to Trp 609) identified in FIG. 14. The gene fragment was synthesized using the method of oligonucleotide directed double-stranded break repair as disclosed in U.S. patent application Ser. No. 883,242 filed Jul. 8, 1986, which is incorporated herein by reference. The five DNA fragments comprising the TMP gene fragment were ligated together and cloned at the HindIII-SalI sites of pUC19 (FIG. 15). A clone, designated pJC22, was identified by restriction mapping and its primary nucleotide sequence confirmed. The clone pJC22 was digested with HindIII-Asp718 to release a 361bp fragment containing the synthetic HIV-2 TMP gene fragment which was ligated into the HindIII-Asp718 sites of plasmid pTB210 and transformed into XL1 cells. A clone, designated pJC100, was isolated and restriction mapped to identify the hybrid gene of kdsB and HIV-2 TMP.

B. Characterization of fusion protein encoded by pJC100

Figure 16:
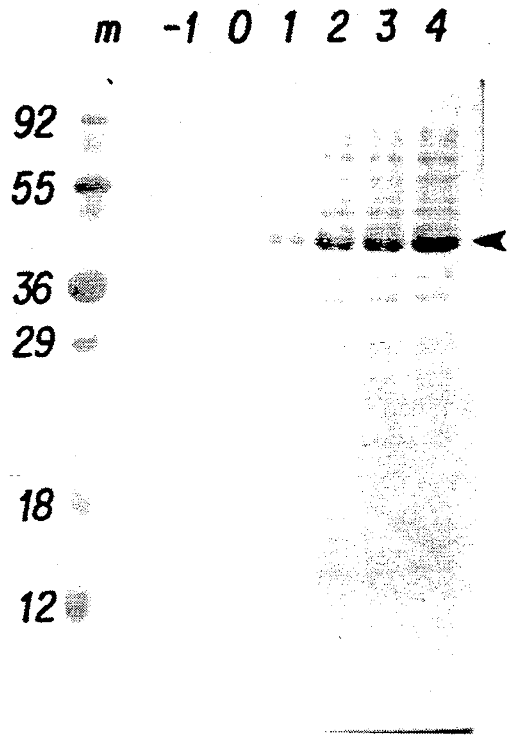
FIG. 16 is a Coomassie brilliant blue stained gel of clone pJC100 induced for the specified time in hours. M is protein molecular weight markers.

Fifty-mL of LB/Amp in a 250 mL flask was inoculated with 500 1 of an overnight culture of either pTB210/XL1 or pJC100/XL1 and allowed to shake at 37° C. until the $OD_{600}$ reached 0.5 absorbance units (1.5–2.0 hours) at which time IPTG was added to a final concentration of 1 mM. An aliquot (1.5 mL) of the culture was removed every hour for four hours and then a final aliquot taken at 18 hours post induction. These aliquots were pelleted and lysed in an appropriate volume of 1X treatment buffer to give a final concentration of cells of 10 $OD_{600}$ absorbance units. Aliquots of each timepoint (15 μL) were electrophoresed on 12.5% SDS/PAGE gels and transferred electrophoretically to nitrocellulose Immunoblotting was carried out as described in Example 3B using HIV-2 positive human sera or goat antibody directed against CKS. The HIV-2 positive human sera demonstrated no signal to the pTB210/XL1 culture and a strong signal to the pJC100/XL1 culture at the expected molecular weight. The goat antibody against CKS reacted strongly with both cultures at the expected molecular weights. A similar SDS/PAGE gel was run and Coomassie blue staining demonstrated that expression of the fusion protein peaked at 3–4 hours post induction at a level of 15% of total protein. FIG. 16 demonstrates the expression of the CKS/HIV-2 TMP fusion protein in a ten liter fermenter as seen by Coomassie blue staining of a 12.5% SDS/PAGE gel of various time points before and after induction. A partial purification of the fusion protein was obtained by the method described in Example 5B with similar results.

EXAMPLE 11

CKS-Core

A. Construction of Plasmid pJO200

The cloning vector pJO200 allows the fusion of recombinant proteins to the CKS protein. The plasmid consists of the plasmid pBR322 with a modified lac promoter fused to a kdsB gene fragment (encoding the first 239 of the entire 248 amino acids of the *E. coli* CMP-KDO synthetase of CKS protein), and a synthetic linker fused to the end of the kdsB gene fragment. The cloning vector pJO200 is a modification of vector pTB210. The synthetic linker includes: multiple restriction sites for insertion of genes; translational stop signals, and the trpA rho-independent transcriptional terminator. The CKS method of protein synthesis as well as CKS vectors including pTB210 are disclosed in U.S. patent application Ser. Nos. 167,067 and 276,263, filed Mar. 11, 1988 and Nov. 23, 1988, respectively, which enjoy common ownership and incorporated herein by reference.

B. Preparation of HCV CKS-Core Expression Vector

Figure 17:
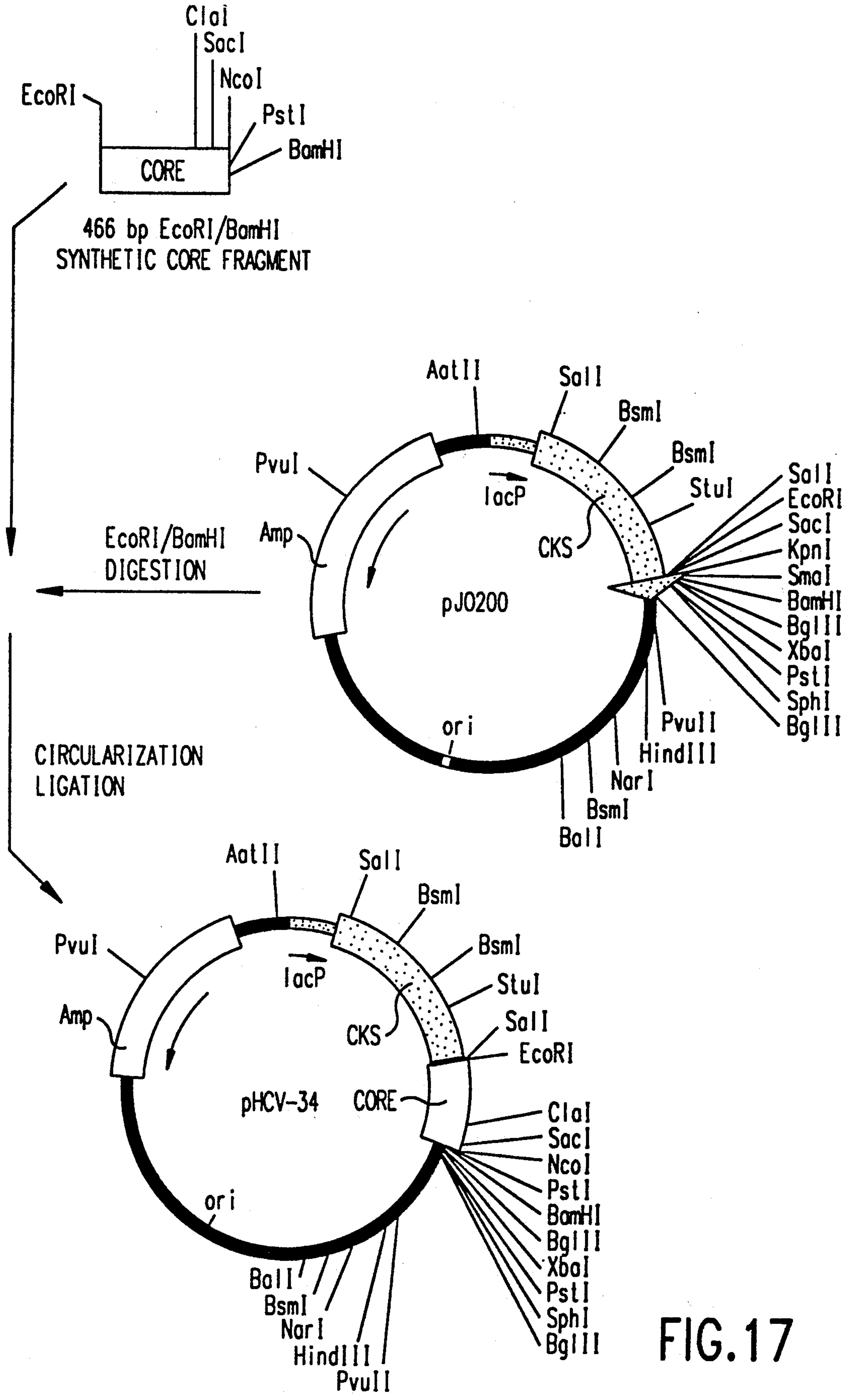
FIG. 17 represents the CKS fusion vector pJ0200.
Figure 19:
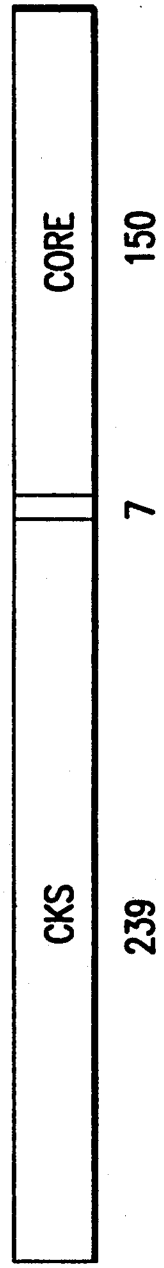
FIG. 19 represents the HCV CKS-core.

Six individual nucleotides representing amino acids 1–150 of the HCV genome were ligated together and cloned as a 466 base pair EcoR1-BamH1 fragment into the CKS fusion vector pJO200 as presented in FIG. 17. The complete DNA sequence of this plasmid, designated pHCV-34, and the entire amino acid sequence of the pHCV-34 recombinant antigen produced is presented in FIG. 18. The resultant fusion protein HCV CKS-Core, consists of 239 amino acids of CKS, seven amino acids contributed by linker DNA sequences, and the first 150 amino acids of HCV as illustrated in FIG. 19.

The pHCV-34 plasmid and the CKS plasmid pTB210 were transformed into *E. coli* K-12 strain xL-1 (recA1, endA1, gyrA96, thi-1, hsdR17, supE44, relA1, lac/F', proAB, laclqZDM15, TN10) cells made competent by the calcium chloride method. In these constructions the expression of the CKS fusion proteins was under the control of the lac promoter and was induced by the addition of IPTG. These plasmids replicated as independent elements, were nonmobilizable and were maintained at approximately 10–30 copies per cell.

C. Characterization of Recombinant HCV-Core

In order to establish that clone pHCV-34 expressed the unique HCV-CKS Core protein, the pHCV-34/XL-1 culture was grown overnight at 37° C. in growth media consisting of yeast extract, trytone, phosphate salts, glucose and ampicillin. When the culture reached an OD600 of 1.0, IPTG was added to a final concentration of 1 mM to induce expression. Samples (1.5 mL) were removed at 1 hour intervals, and cells were pelleted and resuspended to an OD600 of 1.0 in 2X SDS/PAGE loading buffer. Aliquots (15 μL) of the prepared samples were separated on duplicate 12.5% SDS/PAGE gels.

One gel was fixed in a solution of 50% methanol and 10% acetic acid for 20 minutes at room temperature, and then stained with 0.25% Coomassie blue dye in a solution of 50% methanol and 10% acetic acid for 30 minutes. Destaining was carried out using a solution of 10% methanol and 7% acetic acid for 3–4 hours, or until a clear background was obtained.

Figure 20:
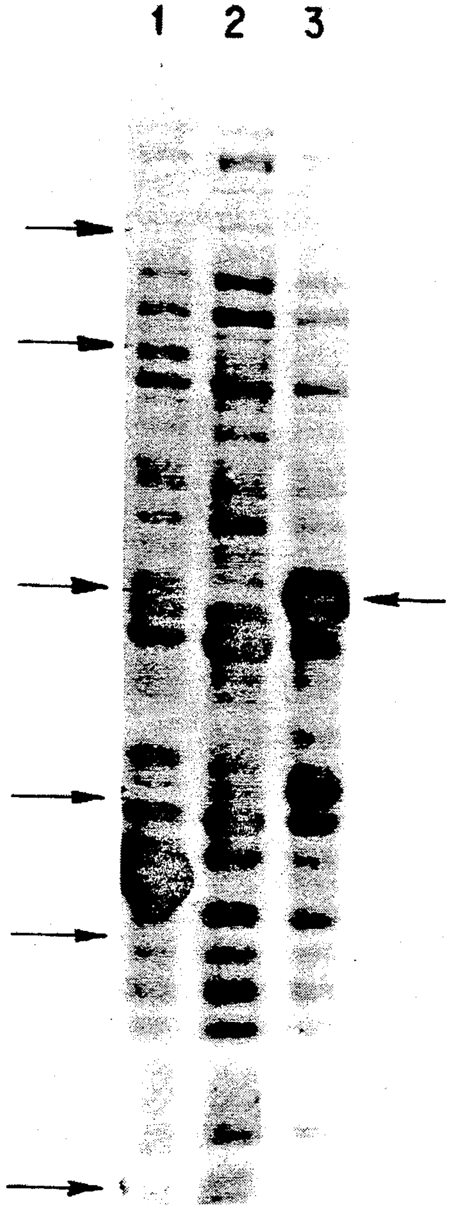
FIG. 20 represents the expression of pHCV-34 proteins in *E. coli.*

FIG. 20 presents the expression of pHCV-34 proteins in *E. coli*. Molecular weight standards were run in Lane M. Lane 1 contains the plasmid pJO200-the CKS vector without the HCV sequence. The arrows on the left indicate the mobilities of the molecular weight markers from top to bottom: 110,000; 84,000; 47,000; 33,000; 24,000 and 16,000 daltons. The arrows on the right indicate the mobilities of the recombinant HCV proteins. Lane 2 contains the *E. coli* lysate containing pHCV-34 expressing CKS-Core (amino acids 1 to 150) prior to induction; and Lane 3 after 3 hours of induction. The results show that the recombinant protein pHCV-34 has an apparent mobility corresponding to a molecular size of 48,000 daltons. This compares acceptably with the predicted molecular mass of 43,750 daltons.

Proteins from the second 12.5% SDS/PAGE gel were electrophoretically transferred to nitrocellulose for immunoblotting. The nitrocellulose sheet containing the transferred proteins was incubated with Blocking Solution for one hour and incubated overnight at 4° C. with HCV patients' sera diluted in TBS containing *E. coli* K-12 strain XL-1 lysate. The nitrocellulose sheet was washed three times in TBS, then incubated with HRPO-labeled goat anti-human IgG, diluted in TBS containing 10% fetal calf sera. The nitrocellulose was washed three times with TBS and the color was developed in TBS containing 2 mg/mL 4-chloro-1-napthol, 0.02% hydrogen peroxide and 17% methanol. Clone HCV-34 demonstrated a strong immunoreactive band at 48,000 daltons with the HCV patients' sera. Thus, the major protein in the Coomassie stained protein gel was immunoreactive. Normal human serum did not react with any component of pHCV-34.

EXAMPLE 12

HCV CKS-33c-BCD

A. Preparation of HCV CKS-33c-BCD Expression Vector

The construction of this recombinant clone expressing the HCV CKS-33-BCD antigen was carried out in three steps described below. First, a clone expressing the HCV CKS-BCD antigen was constructed, designated pHCV-23. Second, a clone expressing the HCV CKS-33 antigen was constructed, designated pHCV-29. Lastly, the HCV BCD region was excised from pHCV-23 and inserted into pHCV-29 to construct a clone expressing the HCV CKS-33-BCD antigen, designated pHCV-31.

Figure 21:
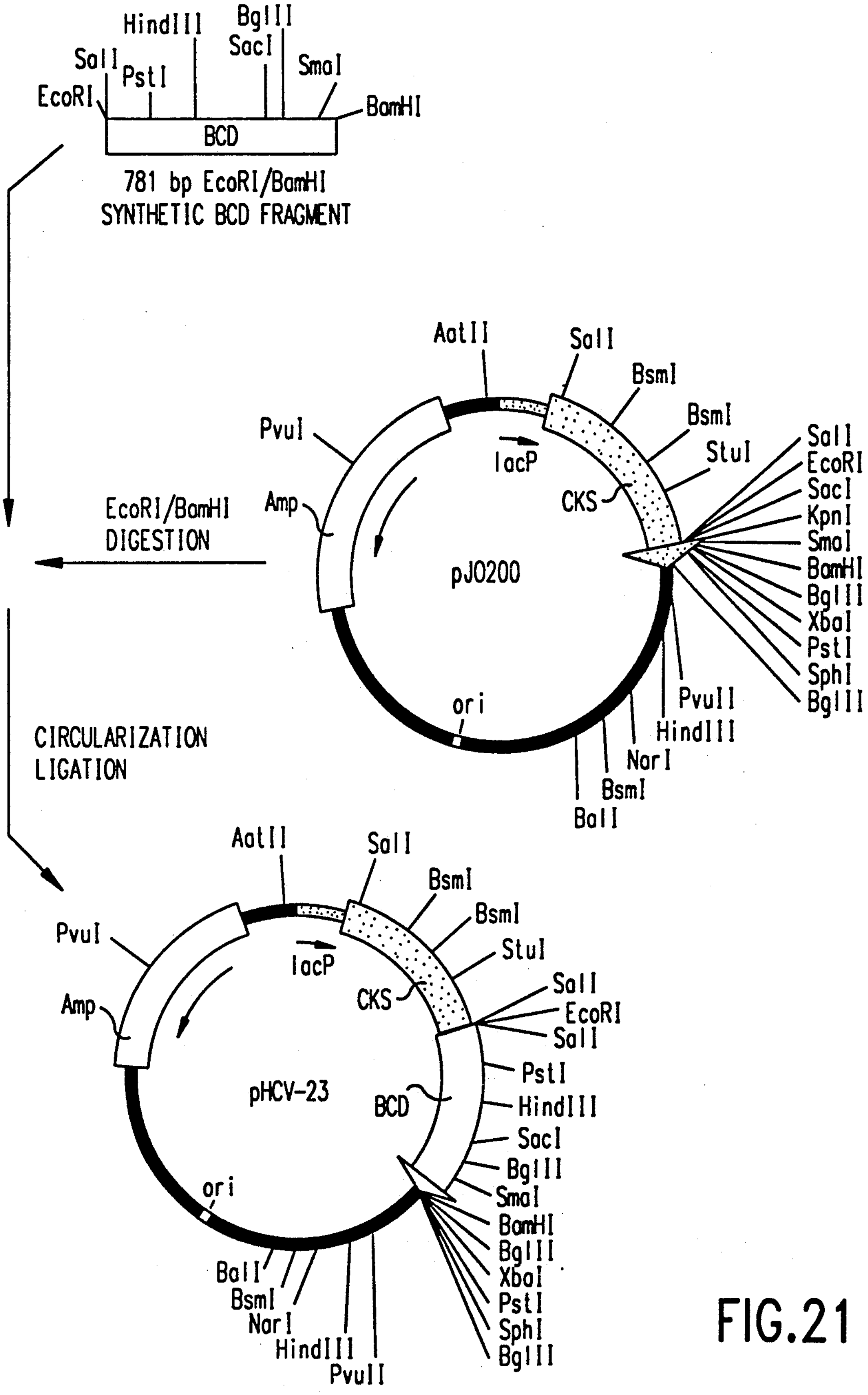
FIG. 21 represents ligation and cloning of CKS fusion vector pJ0200 with a 781 base pair EcoRl-BamHl fragment.

To construct the plasmid pHCV-23, thirteen individual oligonucleotides representing amino acids 1676–1931 of the HCV genome were ligated together and cloned as three separate EcoR1-BamH1 subfragments into the CKS fusion vector pJ0200. After subsequent DNA sequence confirmation, the three subfragments, designated B, C and D respectively, were digested with the appropriate restriction enzymes, gel purified, ligated together, and cloned as a 781 base pair EcoRl-BamHl fragment in the CKS fusion vector pJ0200, as illustrated in FIG. 21. The resulting plasmid, designated pHCV-23, expresses the HCV CKS-BCD antigen under control of the lac promoter. The HCV CKS-BCD antigen consists of 239 amino acids of CKS, seven amino acids contributed by linker DNA sequences, 256 amino acids from the HCV NS4 region (amino acids 1676–19310), and 10 additional amino acids contributed by linker DNA sequences.

Figure 22:
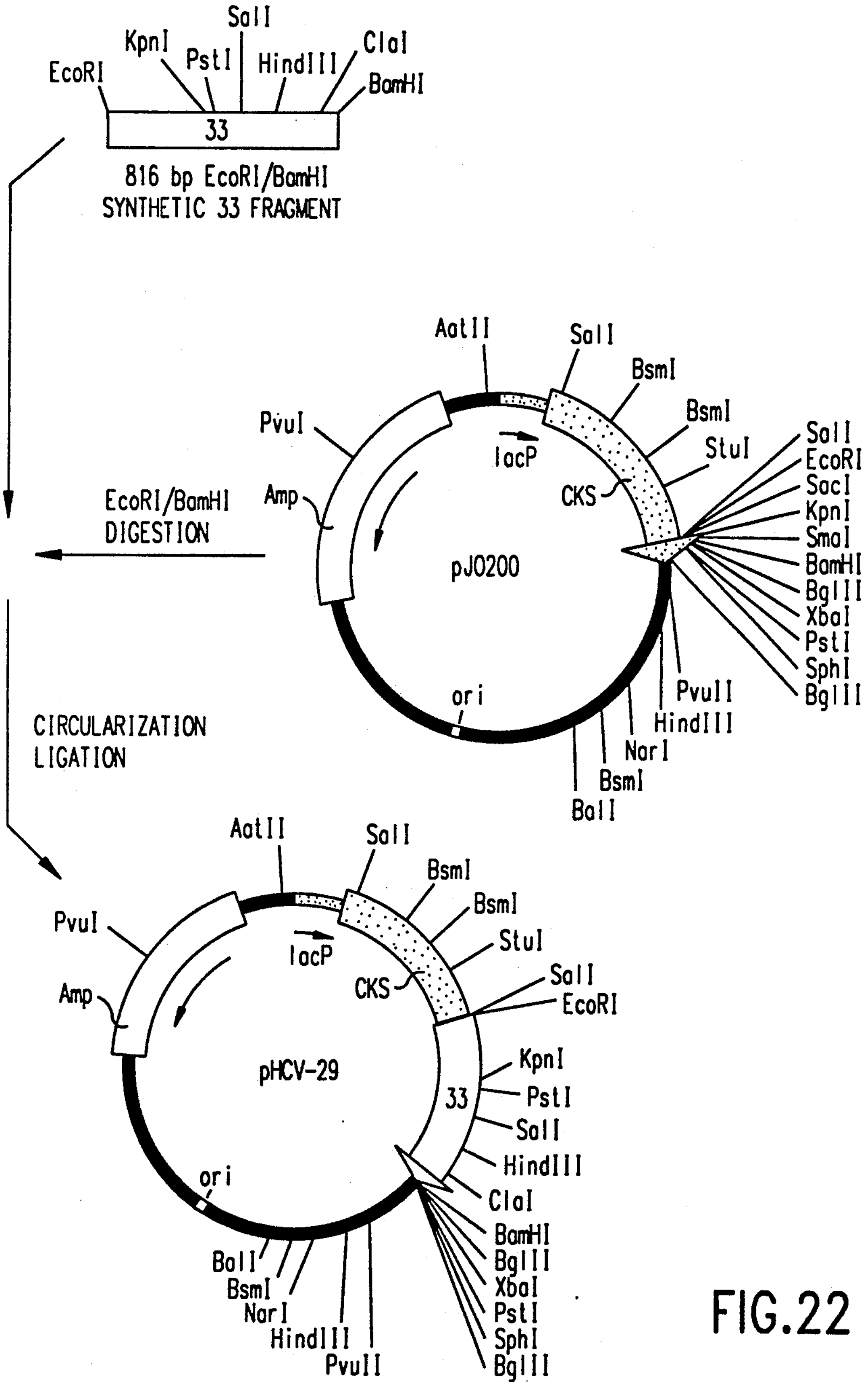
FIG. 22 represents ligation and cloning of CKS fusion vector pJ0200 with a 816 base pair EcoRl-BamHl fragment.

To construct the plasmid pHCV-29 twelve individual oligonucleotides representing amino acids 1192–1457 of the HCV genome were ligated together and cloned as two separate EcoRl-BamHl subfragments into the CKS fusion vector pJ0200. After subsequent DNA sequence confirmation, the two subfragments were digested with the appropriate restriction enzymes, gel purified, ligated together and cloned again as an 816 base pair EcoRl-BamHl fragment in the CKS fusion vector pJ0200, as illustrated in FIG. 22. The resulting plasmid, designated pHCV-29, expresses the CKS-33 antigen under control of the lac promoter. The HCV CKS-33 antigen consists of 239 amino acids of CKS, eight amino acids contributed by linker DNA sequences, and 266 amino acids from the HCV NS3 region (amino acids 1192–1457).

Figure 23A:
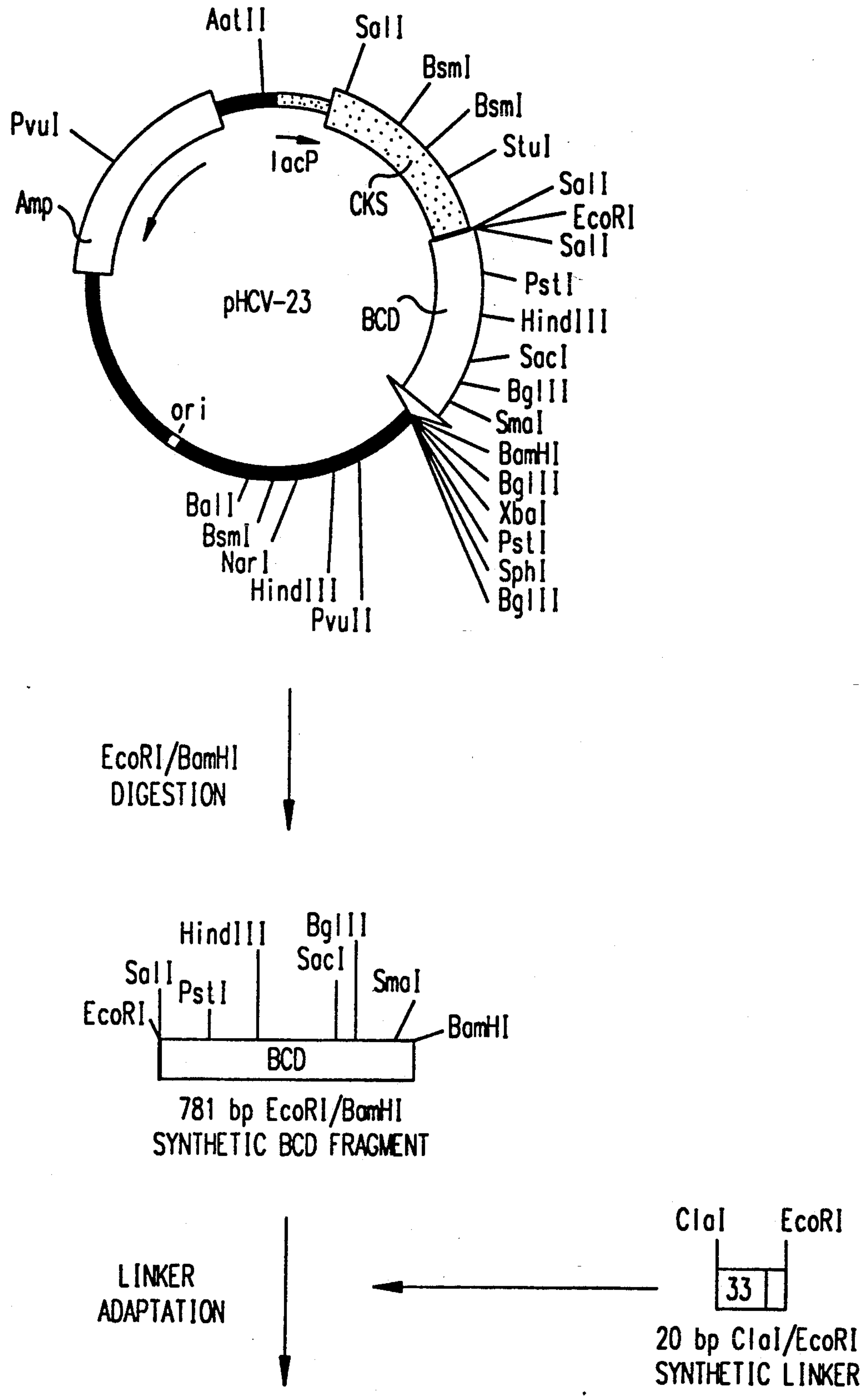
FIG. 23 (Parts A and B) represents the construction of plasmid pHCV-31.
Figure 23B:
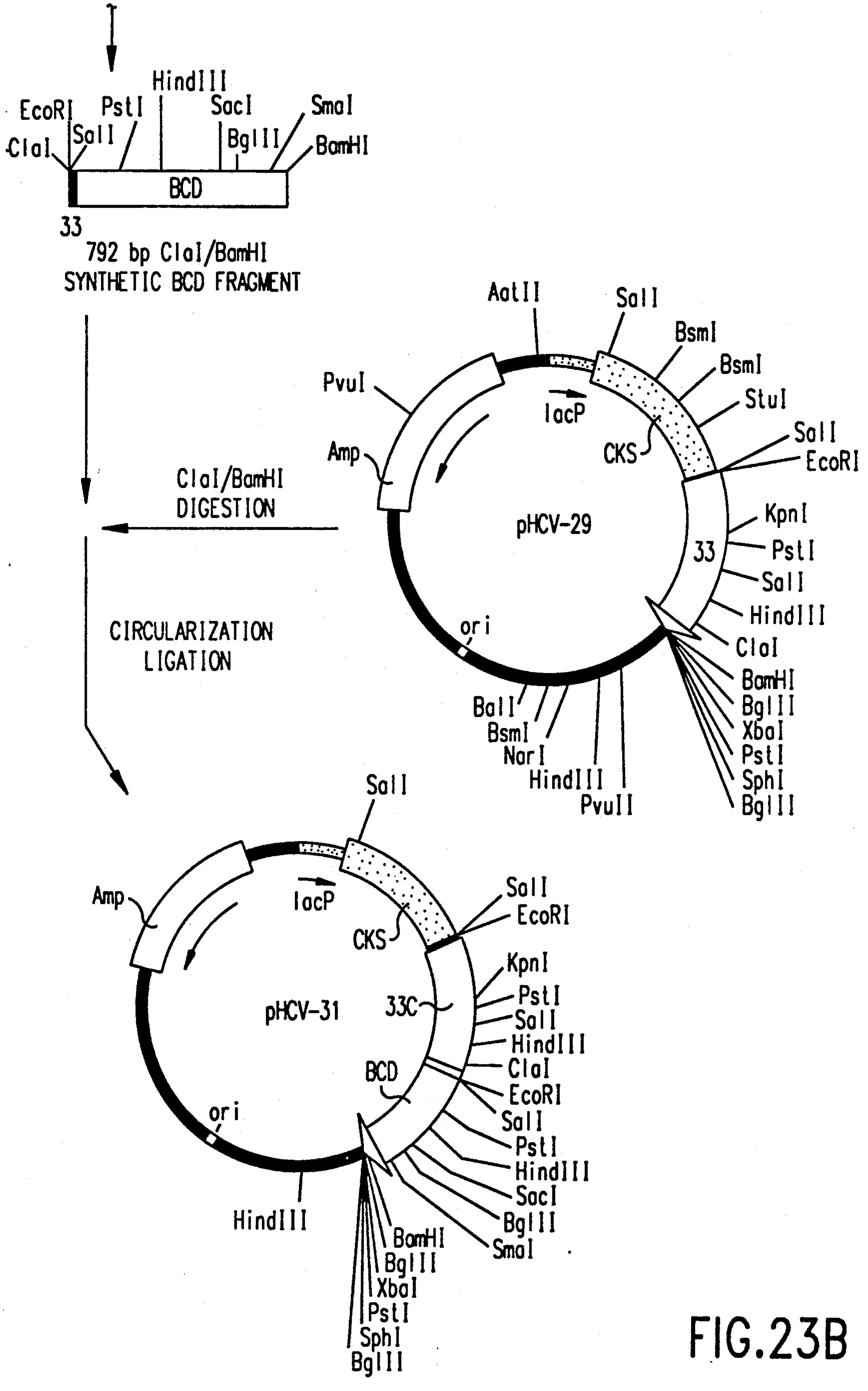
Figure 25:
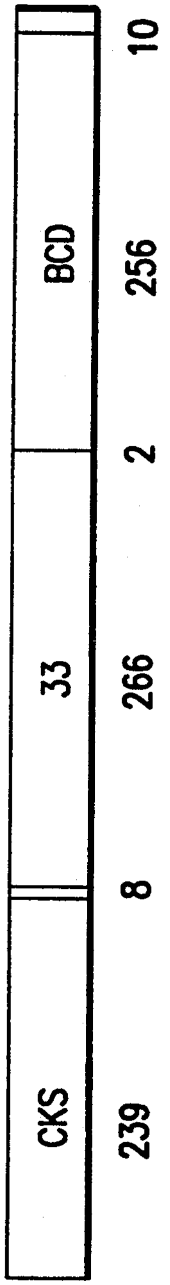
FIG. 25 is a schematic representation of the pHCV-34 and CKS-pTB210 plasmids of Example 1.

To construct the plasmid pHCV-31, the 781 base pair EcoRl-BamHl fragment from pHCV-23 representing the HCV-BCD region was linker-adapted to produce a Clal-BamHl fragment which was the gel purified and ligated into pHCV-29 at the Clal-BamHl sites as illustrated in FIG. 23. The resulting plasmid, designated pHCV-31, expresses the pHCV-31 antigen under control of the lac promoter. The complete DNA sequence of pHCV-31 and the entire amino acid sequence of the HCV CKS-33-BCD recombinant antigen produced is presented in FIG. 24. The HCV CKS-33-BCD antigen consists of 239 amino acids of CKS, eight amino acids contributed by linker DNA sequences, 266 amino acids of the HCV NS3 region (amino acids 1192–1457), 2 amino acids contributed by linker DNA sequences, 256 amino acids of the HCV NS4 region (amino acids 1676–1931), and 10 additional amino acids contributed by linker DNA sequences. FIG. 25 presents a schematic representation of the pHCV-31 antigen.

The pHCV-31 plasmid was transformed into *E. coli* K-12 strain XL-1 in a manner similar to the pHCV-34 and CKS-pTB210 plasmids of Example 1.

B. Characterization of Recombinant HCV CKS-33-BCD

Figure 26:
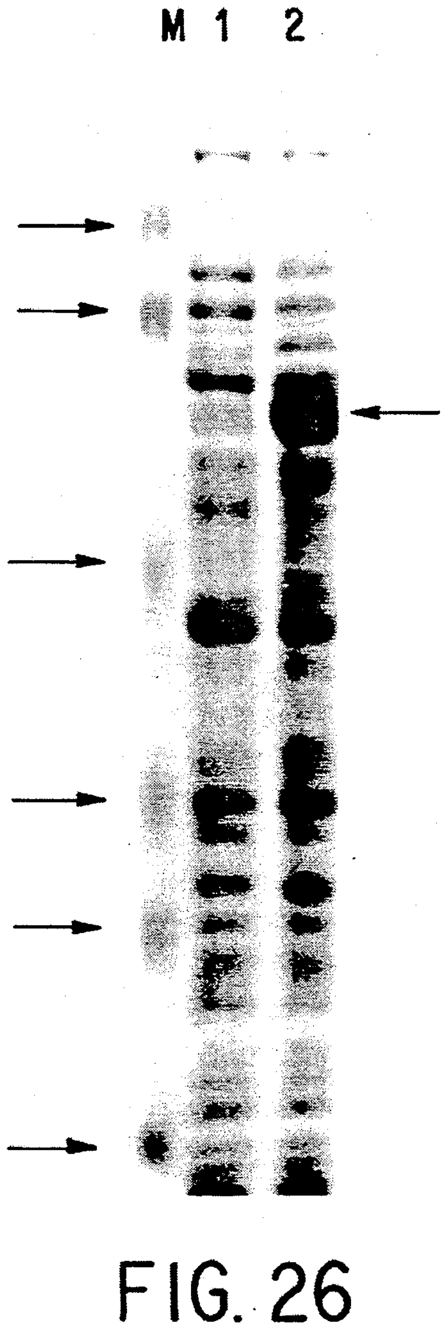
FIG. 26 represents SDS/PAGE gels for the characterization of pHCV-33-BCD containing plasmid pHCV-29.

Characterization of pHCV CKS-33-BCD was carried out in a manner similar to pHCV CKS-Core of Example 1. pHCV-23, pHCV SDS/PAGE gels were run for *E. coli* lysates containing the plasmids pHCV-29 (FIG. 26), pHCV-23 (FIG. 27), and pHCV-31 (FIG. 28) expressing the recombinant fusion proteins CKS-33c, CKS-BCD and CKS-33-BCD, respectively. For all three figures, molecular weight standards were run in Lane M, with the arrows on the left indicating the mobilities of the molecular weight markers from top to bottom: 110,000; 84,000; 47,000; 33,000; 24,000 and 16,000 daltons. In FIG. 26, Lane 1 contained the *E. coli* lysate containing pHCV-29 expressing HCV CKS-33c (amino acids 1192–1457) prior to induction and Lane 2 after 4 hours induction. These results show that the recombinant pHCV-29 fusion protein has an apparent mobility corresponding to a molecular size of 60,000 daltons. This compares acceptably to the predicted molecular mass of 54,911.

Figure 27:
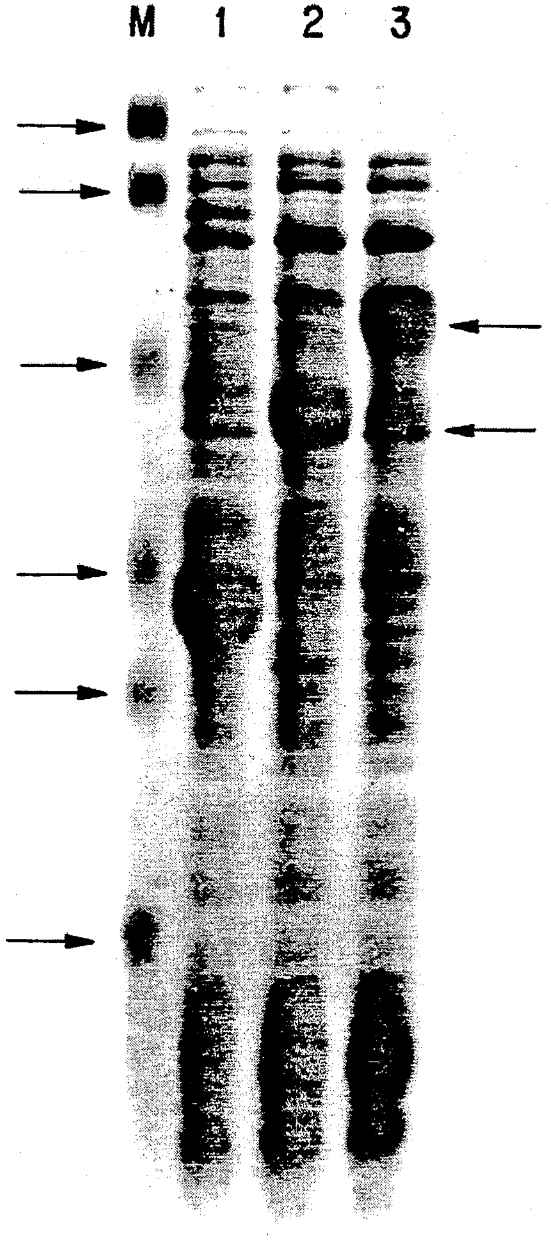
FIG. 27 represents SDS/PAGE gels for the characterization of pHCV-33-BCD containing plasmid pHCV-23.

In FIG. 27, Lane 1 contained the *E. coli* lysate containing pJ0200, the CKS vector without the HCV sequence. Lane 2, contained pHCV-20 expressing the HCV CKS-B (amino acids 1676–1790). Lane 3 contained the fusion protein pHCV-23 (amino acids 1676–1931). These results show that the recombinant pHCV-23 fusion protein has an apparent mobility corresponding to a molecular size of 55,000 daltons. This compares acceptably to the predicted molecular mass of 55,070 daltons.

Figure 28:
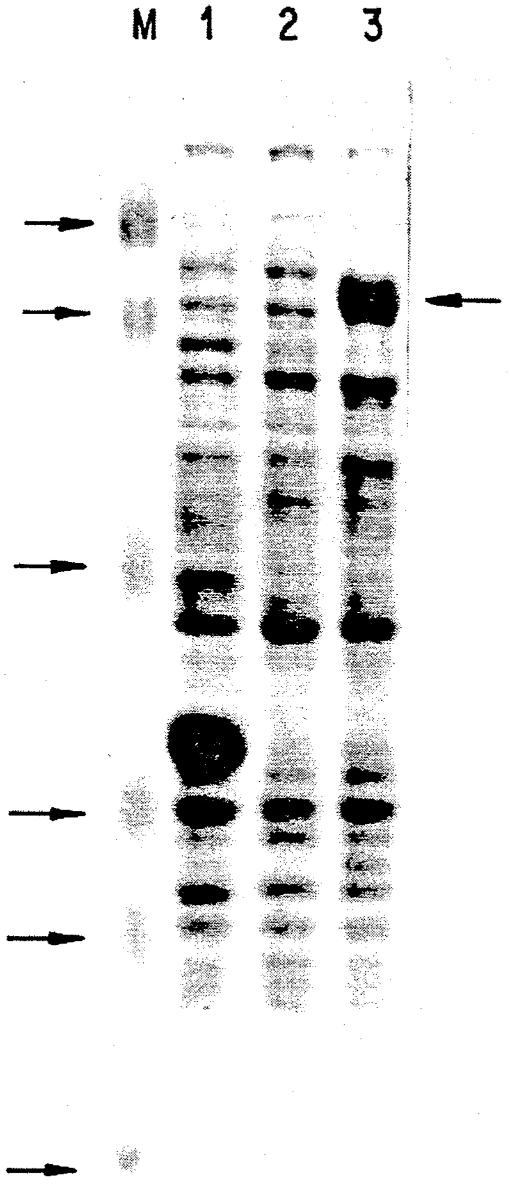
FIG. 28 represents SDS/PAGE gels for the characterization of pHCV-33-BCD containing plasmid pHCV-31.

In FIG. 28, Lane 1 contained the *E. coli* lysate containing pJ0200, the CKS vector without the HCV sequences. Lane 2 contained pHCV-31 expressing the CKS-33c-BCD fusion protein (amino acids 1192–1447 and 1676–1931) prior to induction and Lane 3 after 2 hours induction. These results show that the recombinant pHCV-31 (CKS-33c-BCD) fusion protein has an apparent mobility corresponding to a molecular size of 90,000 daltons. This compares acceptably to the predicted molecular mass of 82,995 daltons.

An immunoblot was also run on one of the SDS/PAGE gels derived from the pHCV-31/X1-1 culture. Human serum from an HCV exposed individual reacted strongly with the major pHCV-31 band at 90,000 daltons. Normal human serum did not react with any component of the pHCV-31 (CKS-33-BCD) preparations.

It will be apparent that many modifications and variations of the present invention as herein set forth are possible without departing from the spirit and scope hereof, and that, accordingly, such limitations are imposed only as indicated by the appended claims.

What is claimed is:

1. A method for expressing HCV protein in a prokaryotic cell, said method comprising the steps of:

(a) providing a DNA vector having:

1) a control region, said control region comprising a prokaryotic promoter and a prokaryotic binding site, wherein said control region directs expression of a DNA sequence comprising two elements operatively linked in a 5' to 3' direction, a first element encoding CKS protein; and 2) a second element encoding said HCV protein, wherein said two elements are contiguous and in the same reading frame;

(b) transforming said prokaryotic cell with said DNA vector; and (c) expressing a fusion protein of CKS protein and said HCV protein.

2. The method of claim 1 wherein said DNA vector includes an additional region located between said CKS region and said region encoding said HCV protein to be expressed, wherein said additional region encodes a set of 1 to about 3 amino acids for site-specific chemical or enzymatic cleavage of said fusion protein.

3. The method of claim 1 wherein said prokaryotic promoter is a lacP-T9-D23 promoter comprising the sequence:

ATTAATGTGAGTTAGCTCACTCATTAGG-CACCCCAGGCTTTACACTTTATG-TTCCGGCTCGTATTTTGTGTGG.

4. The method of claim 1 wherein said HCV protein is capable reacting with appropriate antiserum.

5. The method of claim 4 wherein said HCV protein is encoded by the viral genome of HCV which is capable of reacting with appropriate antiserum.

6. The method of claim 1 wherein said DNA vector is provided by:

a) providing plasmid DNA having a lacP-T9-D23 promoter;

b) inserting a gene encoding CKS protein under the transcriptional-level control of said lacP-T9D-23 promoter; and c) inserting a DNA region encoding for said HCV protein to be expressed at about the 3' end of said CKS gene wherein the final fusion product comprises said HCV protein to be expressed and CKS protein.

7. A cloning vector for transforming cells to express heterologous HCV protein, said cloning vector comprising a plasmid having a prokaryotic control region comprising a prokaryotic promoter and a prokaryotic ribosome binding site, wherein said control region directs expression of a DNA sequence comprising two elements operatively linked in a 5' to 3' direction, a first element and a second element encoding CKS protein and said HCV protein to be expressed, wherein said two elements are contiguous and in the same reading frame.

8. The cloning vector of claim 7 wherein said promoter is a sequence substantially homologous to lacP-T9-D23 promoter comprising:

ATTAATGTGAGTTAGCTCACTCATTAGG-CACCCAGGCTTTACACTTTATG-TTCCGGCTCGTATTTTGTGTGG.

9. A gene sequence for insertion into a plasmid vector, said gene sequence comprising in a 5' to 3' direction:

a) a prokaryotic promoter;

b) a prokaryotic ribosome binding site;

c) a first gene fragment encoding CKS protein; and d) a second gene fragment encoding HCV protein to be expressed, wherein said first and second gene fragments are contiguous and in the same reading frame.

10. The gene sequence of claim 9 wherein said promoter is a synthetic promoter.

11. The gene sequence of claim 10 wherein said promoter is a lacP-T9-D23 promoter comprising the sequence:

ATTAATGTGAGTTAGCTCACTCATTAGG-CACCCCAGGCTTTACACTTTATG-TTCCGGCTCGTATTTTGTGTGG.

12. The gene sequence of claim 9 wherein said ribosome binding site is TAAGGAGGT.

13. The gene sequence of claim 9 wherein said first and second gene fragment are joined by a linker gene sequence which encodes for a protein sequence which is cleavable by a site specific chemical or enzymatic agent.

14. The gene sequence of claim 9 wherein said second gene fragment encodes HCV protein which is capable of reacting with appropriate antiserum.

* * * * *